United States Patent

Bouchard et al.

[11] Patent Number: 5,906,990
[45] Date of Patent: May 25, 1999

[54] TAXOIDS, PREPARATION THEREOF, AND PHARMACEUTICAL COMPOSITIONS CONTAINING SAME

[75] Inventors: Hervé Bouchard, Thiais; Alain Commercon, Vitry-sur-Seine, both of France

[73] Assignee: Rhône-Poulenc Rorer S.A., Antony Cedex, France

[21] Appl. No.: 08/930,814

[22] PCT Filed: Apr. 12, 1996

[86] PCT No.: PCT/FR96/00559

§ 371 Date: Oct. 10, 1997

§ 102(e) Date: Oct. 10, 1997

[87] PCT Pub. No.: WO96/32387

PCT Pub. Date: Oct. 17, 1996

[30] Foreign Application Priority Data

Apr. 14, 1995 [FR] France ................................. 95 04559

[51] Int. Cl.⁶ ........................ A61K 31/335; C07D 305/14
[52] U.S. Cl. ......................... 514/449; 549/510; 549/511
[58] Field of Search ........................... 514/449; 549/510, 549/511

[56] References Cited

U.S. PATENT DOCUMENTS

| | | | |
|---|---|---|---|
| 5,254,580 | 10/1993 | Chen et al. | 514/449 |
| 5,294,637 | 3/1994 | Chen et al. | 514/449 |
| 5,395,850 | 3/1995 | Roth | 549/510 |
| 5,532,388 | 7/1996 | Bouchard et al. | 549/510 |
| 5,750,738 | 5/1998 | Bastart et al. | 549/510 |

FOREIGN PATENT DOCUMENTS

WO 95/09163  4/1995  WIPO .

*Primary Examiner*—Amelia Owens
*Attorney, Agent, or Firm*—Finnegan, Henderson, Farabow, Garrett & Dunner, L.L.P.

[57] ABSTRACT

The present invention relates to novel taxoids of general formula:

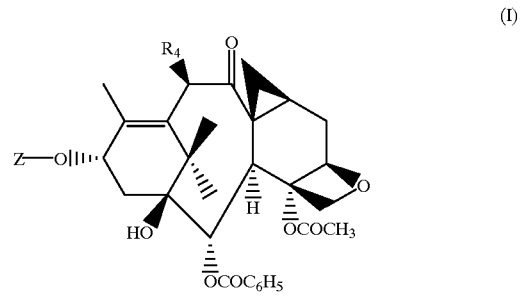

in which:

Z represents a hydrogen atom or a radical of general formula:

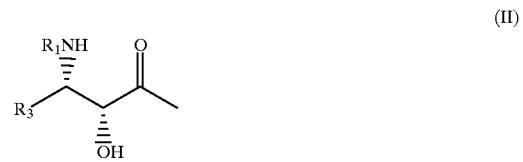

25 Claims, No Drawings

TAXOIDS, PREPARATION THEREOF, AND PHARMACEUTICAL COMPOSITIONS CONTAINING SAME

The present invention relates to novel taxoids of general formula:

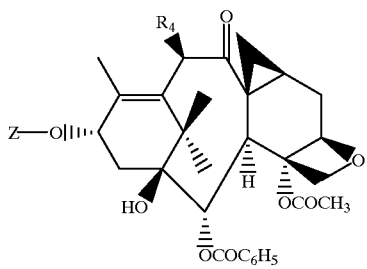

(I)

in which:

Z represents a hydrogen atom or a radical of general formula:

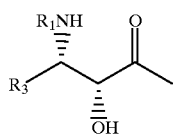

(II)

in which:

R₁ represents a benzoyl radical optionally substituted with one or more atoms or radicals, which may be identical or different, chosen from halogen atoms and alkyl radicals containing 1 to 4 carbon atoms, alkoxy radicals containing 1 to 4 carbon atoms or trifluoromethyl, thenoyl or furoyl radicals or a radical R₂—O—CO— in which R₂ represents:

an alkyl radical containing 1 to 8 carbon atoms, an alkenyl radical containing 2 to 8 carbon atoms, an alkynyl radical containing 3 to 8 carbon atoms, a cycloalkyl radical containing 3 to 6 carbon atoms, a cycloalkenyl radical containing 4 to 6 carbon atoms or a bicycloalkyl radical containing 7 to 10 carbon atoms, these radicals optionally being substituted with one or more substituents chosen from halogen atoms and hydroxyl radicals, alkoxy radicals containing 1 to 4 carbon atoms, dialkylamino radicals in which each alkyl part contains 1 to 4 carbon atoms, piperidino, morpholino or 1-piperazinyl radicals (optionally substituted at −4 with an alkyl radical containing 1 to 4 carbon atoms or with a phenylalkyl radical in which the alkyl part contains 1 to 4 carbon atoms), cycloalkyl radicals containing 3 to 6 carbon atoms, cycloalkenyl radicals containing 4 to 6 carbon atoms, phenyl radicals (optionally substituted with one or more atoms or radicals chosen from halogen atoms and alkyl radicals containing 1 to 4 carbon atoms or alkoxy radicals containing 1 to 4 carbon atoms), cyano or carboxyl radicals or alkoxycarbonyl radicals in which the alkyl part contains 1 to 4 carbon atoms, a phenyl or α- or β-naphthyl radical optionally substituted with one or more atoms or radicals chosen from halogen atoms and alkyl radicals containing 1 to 4 carbon atoms or alkoxy radicals containing 1 to 4 carbon atoms or a 5-membered aromatic heterocyclic radical preferably chosen from furyl and thienyl radicals, or a saturated heterocyclic radical containing 4 to 6 carbon atoms optionally substituted with one or more alkyl radicals containing 1 to 4 carbon atoms, R₃ represents a straight or branched alkyl radical containing 1 to 8 carbon atoms, a straight or branched alkenyl radical containing 2 to 8 carbon atoms, a straight or branched alkynyl radical containing 2 to 8 carbon atoms, a cycloalkyl radical containing 3 to 6 carbon atoms, a phenyl or α- or β-naphthyl radical optionally substituted with one or more atoms or radicals chosen from halogen atoms and alkyl, alkenyl, alkynyl, aryl, aralkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, alkylcarbamoyl, dialkylcarbamoyl, cyano, nitro and trifluoromethyl radicals, or a 5-membered aromatic heterocycle containing one or more hetero atoms, which may be identical or different, chosen from nitrogen, oxygen or sulphur atoms and optionally substituted with one or more substituents, which may be identical or different, chosen from halogen atoms and alkyl, aryl, amino, alkylamino, dialkylamino, alkoxycarbonylamino, acyl, arylcarbonyl, cyano, carboxyl, carbamoyl, alkylcarbamoyl, dialkylcarbamoyl or alkoxycarbonyl radicals, it being understood that, in the substituents of the phenyl, α- or β-naphthyl radicals and aromatic heterocyclic radicals, the alkyl radicals and the alkyl portions of the other radicals contain 1 to 4 carbon atoms and that the alkenyl and alkynyl radicals contain 2 to 8 carbon atoms and that the aryl radicals are phenyl or α- or β-naphthyl radicals.

R₄ represents an alkoxy radical containing 1 to 6 carbon atoms in a straight or branched chain, an alkenyloxy radical containing 3 to 6 carbon atoms in a straight or branched chain, an alkynyloxy radical containing 3 to 6 carbon atoms in a straight or branched chain, a cycloalkyloxy radical containing 3 to 6 carbon atoms, a cycloalkenyloxy radical containing 3 to 6 carbon atoms optionally substituted with one or more halogen atoms or with an alkoxy radical containing 1 to 4 carbon atoms, an alkylthio radical containing 1 to 4 carbon atoms or a carboxyl radical, an alkyloxycarbonyl radical in which the alkyl part contains 1 to 4 carbon atoms, a cyano or carbamoyl radical, an N-alkylcarbamoyl or N,N-dialkylcarbamoyl radical in which each alkyl part contains 1 to 4 carbon atoms or forms, with the nitrogen atom to which it is attached, a 5- or 6-membered saturated heterocyclic radical optionally containing a second hetero atom chosen from oxygen, sulphur or nitrogen atoms optionally substituted with an alkyl radical containing 1 to 4 carbon atoms or a phenyl radical or a phenylalkyl radical in which the alkyl part contains 1 to 4 carbon atoms.

The aryl radicals which may be represented by R₃ are preferably phenyl or α- or β-naphthyl radicals optionally substituted with one or more atoms or radicals chosen from halogen atoms (fluorine, chlorine, bromine and iodine) and alkyl, alkenyl, alkynyl, aryl, aralkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, dialkylcarbamoyl, cyano, nitro and trifluoromethyl radicals, it being understood that the alkyl radicals and the alkyl portions of the other radicals contain 1 to 4 carbon atoms, that the alkenyl and alkynyl radicals contain 2 to 8 carbon atoms and that the aryl radicals are phenyl or α- or β-naphthyl radicals.

The heterocyclic radicals which may be represented by $R_3$ are preferably 5-membered aromatic heterocyclic radicals containing one or more atoms, which may be identical or different, chosen from nitrogen, oxygen or sulphur atoms, optionally substituted with one or more substituents, which may be identical or different, chosen from halogen atoms (fluorine, chlorine, bromine and iodine) and alkyl radicals containing 1 to 4 carbon atoms, aryl radicals containing 6 to 10 carbon atoms, alkoxy radicals containing 1 to 4 carbon atoms, aryloxy radicals containing 6 to 10 carbon atoms, amino radicals, alkylamino radicals containing 1 to 4 carbon atoms, dialkylamino radicals in which each alkyl part contains 1 to 4 carbon atoms, acylamino radicals in which the acyl part contains 1 to 4 carbon atoms, alkoxycarbonylamino radicals containing 1 to 4 carbon atoms, acyl radicals containing 1 to 4 carbon atoms, arylcarbonyl radicals in which the aryl part contains 6 to 10 carbon atoms, cyano, carboxyl and carbamoyl radicals, alkylcarbamoyl radicals in which the alkyl part contains 1 to 4 carbon atoms, dialkylcarbamoyl radicals in which each alkyl part contains 1 to 4 carbon atoms or alkoxy carbonyl radicals in which the alkoxy part contains 1 to 4 carbon atoms.

The radical $R_4$ preferably represents a is straight or branched alkoxy radical containing 1 to 6 carbon atoms optionally substituted with a methoxy, ethoxy, methylthio, ethylthio, carboxyl, methoxycarbonyl, ethoxycarbonyl, cyano, carbamoyl, N-methylcarbamoyl, N-ethylcarbamoyl, N,N-dimethylcarbamoyl, N,N-diethylcarbamoyl, N-pyrrolidinocarbonyl, N-piperidinocarbonyl or phenyl radical.

The present invention relates more particularly to products of general formula (I) in which Z represents a hydrogen atom or a radical of general formula (II) in which $R_1$ represents a benzoyl radical or a radical $R_2$—O—CO— in which $R_2$ represents a tert-butyl radical and $R_3$ represents an alkyl radical containing 1 to 6 carbon atoms, an alkenyl radical containing 2 to 6 carbon atoms, a cycloalkyl radical containing 3 to 6 carbon atoms, a phenyl radical optionally substituted with one or more atoms or radicals, which may be identical or different, chosen from halogen atoms (fluorine and chlorine) and alkyl (methyl), alkoxy (methoxy), dialkylamino (dimethylamino), acylamino (acetylamino), alkoxycarbonylamino (tert-butoxycarbonylamino) or trifluoromethyl radicals or a 2- or 3-furyl or 2- or 3-thienyl or 2-, 4- or 5-thiazolyl radical and $R_4$ represents a straight or branched alkyloxy radical containing 1 to 6 carbon atoms.

Even more particularly, the present invention relates to the products of general formula (I) in which Z represents a hydrogen atom or a radical of general formula (II) in which $R_1$ represents a benzoyl radical or a radical $R_2$—O—CO— in which $R_2$ represents a tert-butyl radical and $R_3$ represents an isobutyl, isobutenyl, butenyl, cyclohexyl, phenyl, 2-furyl, 3-furyl, 2-thienyl, 3-thienyl, 2-thiazolyl, 4-thiazolyl or 5-thiazolyl radical and $R_4$ represents a methoxy or ethoxy radical.

The products of general formula (I) in which Z represents a radical of general formula (II) exhibit noteworthy antitumour and antileukaemia properties.

According to the present invention, the novel products of general formula (I), in which Z represents a radical of general formula (II), may be obtained by esterification of a product of general formula:

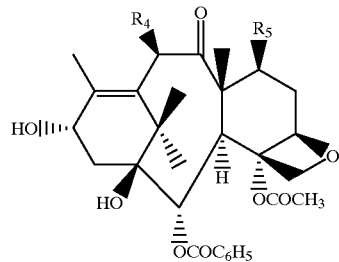

(III)

in which $R_4$ is defined as above and $R_5$ represents a trifluoromethanesulphonyloxy radical or forms a bond with the carbon atom of the α-methyl radical, so as to form a cyclopropane ring, using an acid of general formula:

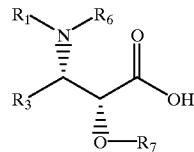

(IV)

in which $R_1$ and $R_3$ are defined as above, or alteratively $R_6$ represents a hydrogen atom and $R_7$ represents a protecting group for the hydroxyl function, and either $R_6$ and $R_7$ together form a 5- or 6-membered saturated heterocycle, or esterification of a derivative of this acid, in order to obtain an ester of general formula:

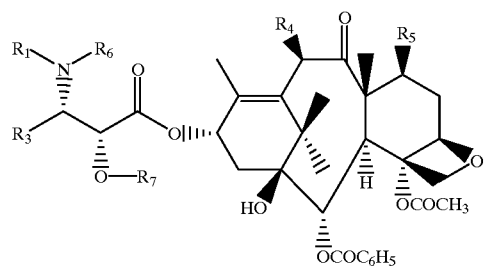

(V)

in which $R_1$, $R_3$, $R_4$, $R_5$, $R_6$ are defined as above, followed by replacement of the protecting groups represented by $R_7$ and/or $R_6$ and $R_7$ by hydrogen atoms and, when $R_5$ represents a trifluoromethanesulphonyloxy radical, removal of this radical so as to form a cyclopropane ring with the carbon atom of the α-methyl radical.

Esterification using an acid of general formula (IV) may be carried out in the presence of a coupling agent (carbodjimide or reactive carbonate) and an activating agent (aminopyridines) in an organic solvent (ether, ester, ketones, nitriles, aliphatic hydrocarbons, halogenated aliphatic hydrocarbons or aromatic hydrocarbons) at a temperature of between −10 and 90° C.

The esterification may also be performed using the acid of general formula (IV) in symmetrical anhydride form, working in the presence of an activating agent (aminopyridines) in an organic solvent (ethers, esters, ketones, nitriles, aliphatic hydrocarbons, halogenated aliphatic hydrocarbons or aromatic hydrocarbons) at a temperature of between 0 and 90° C.

The esterification may also be performed using the acid of general formula (IV) in the form of the halide or in the form of the mixed anhydride with an aliphatic or aromatic acid, optionally prepared in situ, in the presence of a base (tertiary aliphatic amine), working in an organic solvent (ethers, esters, ketones, nitriles, aliphatic hydrocarbons, halogenated aliphatic hydrocarbons or aromatic hydrocarbons) at a temperature of between 0 and 80° C.

Preferably, $R_6$ represents a hydrogen atom and $R_7$ represents a protecting group for the hydroxyl function or alternatively $R_6$ and $R_7$ together form a 5- or 6-membered saturated heterocycle.

When $R_6$ represents a hydrogen atom, $R_7$ preferably represents a methoxymethyl, 1-ethoxyethyl, benzoyloxymethyl, trimethylsilyl, triethylsilyl, β-trimethylsilylethoxymethyl, benzyloxycarbonyl or tetrahydropyranyl radical.

When $R_6$ and $R_7$ together form a heterocycle, this is preferably an oxazolidine ring optionally mono-substituted or gem-disubstituted in position -2.

Replacement of the protecting groups $R_7$ and/or $R_6$ and $R_7$ by hydrogen atoms may be carried out depending on their nature, in the following way:

1) when $R_6$ represents a hydrogen atom and $R_7$ represents a protecting group for the hydroxyl function, replacement of the protecting groups by hydrogen atoms is carried out using an inorganic acid (hydrochloric acid, sulphuric acid or hydrofluoric acid) or organic acid (acetic acid, methanesulphonic acid, trifluoromethanesulphonic acid or p-toluenesulphonic acid) used alone or as a mixture, working in an organic solvent chosen from alcohols, ethers, esters, aliphatic hydrocarbons, halogenated aliphatic hydrocarbons, aromatic hydrocarbons or nitriles, at a temperature of between –10 and 60° C., 2) when $R_6$ and $R_7$ together form a 5- or 6-membered heterocycle and more particularly an oxazolidine ring of general formula:

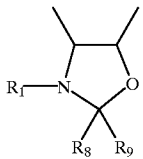

(VI)

in which $R_1$ is defined as above, $R_8$ and $R_9$, which may be identical or different, represent a hydrogen atom or an alkyl radical containing 1 to 4 carbon atoms or an aralkyl radical in which the alkyl part contains 1 to 4 carbon atoms and the aryl part preferably represents a phenyl radical optionally substituted with one or more alkoxy radicals containing 1 to 4 carbon atoms, or an aryl radical preferably representing a phenyl radical optionally substituted with one or more alkoxy radicals containing 1 to 4 carbon atoms, or alternatively $R_8$ represents an alkoxy radical containing 1 to 4 carbon atoms or a trihalomethyl radical such as trichloromethyl or a phenyl radical substituted with a trihalomethyl radical such as trichloromethyl and $R_9$ represents a hydrogen atom, or alternatively $R_8$ and $R_9$ form, together with the carbon atom to which they are attached, a 4- to 7-membered ring, replacement of the protecting group formed by $R_6$ and R7 by hydrogen atoms may be carried out, depending on the meanings of $R_1$, $R_8$ and $R_9$, in the following way:

a) when $R_1$ represents a tert-butoxycarbonyl radical, $R_8$ and $R_9$, which may be identical or different, represent an alkyl radical or an aralkyl (benzyl) or aryl (phenyl) radical, or alternatively $R_8$ represents a trihalomethyl radical or a phenyl radical substituted with a trihalomethyl radical, and $R_9$ represents a hydrogen atom, or alternatively $R_8$ and $R_9$ together form a 4- to 7-membered ring, treatment of the ester of general formula (V) with an inorganic or organic acid, optionally in an organic solvent such as an alcohol, leads to the product of general formula:

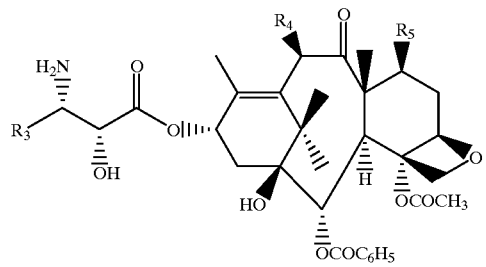

(VII)

in which $R_3$, $R_4$ and $R_5$ are defined as above, which product is acylated using benzoyl chloride in which the phenyl ring is optionally substituted, thenoyl chloride, furoyl chloride or a product of general formula:

$R_2$—O—CO—X (VIII)

in which $R_2$ is defined as above and X represents a halogen atom (fluorine or chlorine) or a residue —O—$R_2$ or —O—CO—O—$R_2$, in order to obtain a product of general formula (I) in which Z represents a radical of general formula (II).

Preferably, the product of general formula (V) is treated with formic acid at a temperature in the region of 20° C., in order to obtain the product of general formula (VII).

Preferably, acylation of the product of general formula (VII) using a benzoyl chloride in which the phenyl radical is optionally substituted, thenoyl chloride or furoyl chloride or a product of general formula (VIII) is carried out in an inert organic solvent chosen from esters such as ethyl acetate, isopropyl acetate or n-butyl acetate and halogenated aliphatic hydrocarbons such as dichloromethane or 1,2-dichloroethane, in the presence of an inorganic base such as sodium bicarbonate or an organic base such as triethylamine. The reaction is carried out at a temperature of between 0 and 50° C., preferably in the region of 20° C.

b) when $R_1$ represents an optionally substituted benzoyl radical, a thenoyl or furoyl radical or a radical $R_2O$—CO— in which $R_2$ is defined as above, $R_8$ represents a hydrogen atom or an alkoxy radical containing 1 to 4 carbon atoms or a phenyl radical substituted with one or more alkoxy radicals containing 1 to 4 carbon atoms and $R_9$ represents a hydrogen atom, replacement of the protecting group formed by $R_6$ and $R_7$ by hydrogen atoms is carried out in the presence of an inorganic acid (hydrochloric acid or sulphuric acid) or an organic acid (acetic acid, methanesulphonic acid, trifluoromethanesulphonic acid or p-toluenesulphonic acid) used alone or as a mixture, in stoichiometric or catalytic amount, working in an organic solvent chosen from alcohols, ethers, esters, aliphatic hydrocarbons, halogenated aliphatic hydrocarbons and aromatic hydrocarbons, at a temperature of between −10 and 60° C., preferably between 15 and 30° C.

Generally, when $R_5$ represents a trifluoromethanesulphonyloxy radical, the product obtained after deprotection is converted into a cyclopropane derivative using an alkali metal halide (sodium iodide or potassium fluoride) or an alkali metal azide (sodium azide) or an ammonium salt, working in an organic solvent chosen from ethers (tetrahydrofuran, diisopropyl ether or methyl t-butyl ether), nitriles (acetonitrile) or aliphatic esters (ethyl acetate), alone or as a mixture, at a temperature of between 20° C. and the boiling point of the reaction mixture.

According to the invention, the products of general formula (III), in which $R_4$ and $R_5$ are defined as above, may be obtained from 10-deacetylbaccatin III of formula:

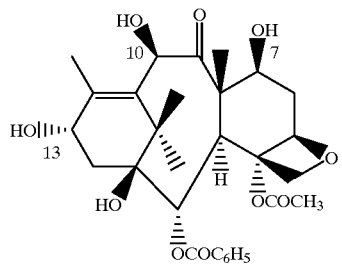
(IX)

It may be particularly advantageous to protect the hydroxyl functions in positions 7 and 13 selectively, for example in the form of a di-silyl ether which may be obtained by the action of a silyl halide of general formula:

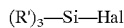
(X)

in which the symbols R', which may be identical or different, represent an alkyl radical containing 1 to 4 carbon atoms optionally substituted with a phenyl radical, or a phenyl radical, on 10-deacetylbaccatin III in order to obtain a product of general formula:

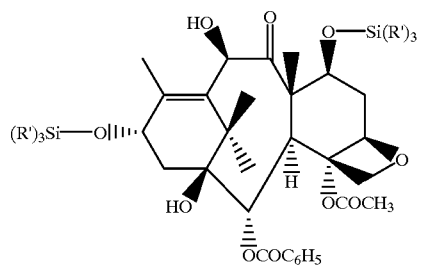
(XI)

in which R' is defined as above, followed by the action of a product of general formula:

(XII)

in which $R'_4$ is such that $R'_4$—O is identical to $R_4$ defined as above and $X_1$ represents a reactive ester residue or a halogen atom, in order to obtain a product of general formula:

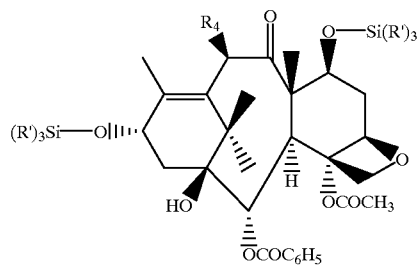
(XIII)

in which R' and $R_4$ are defined as above, the silyl protecting groups of which are replaced by hydrogen atoms in order to obtain a product of general formula:

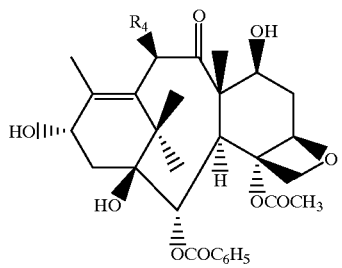
(XIV)

in which $R_4$ is defined as above, which product, on treatment with a trifluoromethanesulphonic acid derivative such as the anhydride or the N-phenyltrifluoromethanesulphonimide, in an inert organic solvent (optionally halogenated aliphatic hydrocarbons or aromatic hydrocarbons) in the presence of an organic base such as an aliphatic tertiary amine (triethylamine) or pyridine, at a temperature of between −50 and +20° C., in order to obtain a product of general formula (III) in which $R_4$ is defined as above and $R_5$ represents a trifluoromethanesulphonyloxy radical, which product, on possible treatment with an alkali metal halide (sodium iodide or potassium fluoride) or an alkali metal azide (sodium azide) or an ammonium salt, working in an organic solvent chosen from ethers (tetrahyrofuran, diisopropyl ether or methyl t-butyl ether), nitrites (acetonitrile) or aliphatic esters (ethyl acetate), alone or as a mixture, at a temperature of between 20° C. and the boiling point of the reaction mixture, leads to a product of general formula (III) in which $R_4$ is defined as above and $R_5$ represents a bond with the carbon atom of the α-methyl radical, so as to form a cyclopropane ring, that is to say a product of general formula (I) in which Z represents a hydrogen atom.

The novel products of general formula (I) obtained by carrying out the processes according to the invention may be purified according to the known methods such as crystallization or chromatography.

The products of general formula (I) in which Z represents a radical of general formula (II) exhibit noteworthy biological properties.

In vitro, measurement of the biological activity is carried out on tubulin extracted from pig brain by the method of M. L. Shelanski et al., Proc. Natl. Acad. Sci. USA, 70, 765–768 (1973). Study of the depolymerization of the microtubules into tubulin is carried out according to the method of G. Chauviere et al., C.R. Acad. Sci., 293, série II, 501–503 (1981). In this study, the products of general formula (I), in which Z represents a radical of general formula (II), prove to be at least as active as taxol and Taxotere.

In vivo, the products of general formula (I) in which Z represents a radical of general formula (II) have proven to be active in mice grafted with B16 melanoma at doses of between 1 and 10 mg/kg intraperitoneally, as well as on other liquid or solid tumours.

The novel products have antitumour properties and more particularly an activity on tumours which are resistant to TAXOL® (Paclitaxel) or to TAXOTERE® (docetaxel). Such tumours comprise tumours of the colon, which have an increased expression of the mdr 1 gene (multi-drug resistance gene). Multi-drug resistance is a common term referring to the resistance of a tumour to various products of varied structure and mechanism of action. Taxoids are generally known to be highly recognized by experimental tumours such as P388/DOX, a cell line selected for its resistance to doxorubicin (DOX) and which overexpresses mdr 1.

The examples which follow illustrate the present invention.

EXAMPLE 1

To a suspension of 0.504 g of 4α-acetoxy-2α-benzoyloxy-5β,20-epoxy-1β,13α-dihydroxy-10β-methoxy-9-oxo-7β-trifluoromethanesulphonyloxy-11-taxene, 0.38 g of (2R,4S,5R)-3-tert-butoxycarbonyl-2-(4-methoxyphenyl)-4-phenyl-1,3-oxazolidine-5-carboxylic acid and 0.1 g of activated powdered 4 Å molecular sieves in 3.2 cm³ of anhydrous toluene are successively added, at a temperature in the region of 20° C., 0.24 g of dicyclohexylcarbodiimide and 30 mg of 4-N,N'-dimethylaminopyridine. After one hour at a temperature in the region of 20° C., the reaction mixture is purified (applied directly to the column) by chromatography at atmospheric pressure on 50 g of silica (0.063–0.2 mm) contained in a column 2.5 cm in diameter (elution gradient: ethyl acetate/dichloromethane from 0/100 to 10/90 by volume), collecting 10 cm³ fractions. The fractions containing only the desired product are combined and concentrated to dryness under reduced pressure (0.27 kPa) at 40° C. for 2 hours. 721.3 mg of 4α-acetoxy-2α-benzoyloxy-5β,20-epoxy-1β-hydroxy-10β-methoxy-9-oxo-7β-trifluoromethanesulphonyloxy-11-taxen-13α-yl (2R,4S,5R)-3-tert-butoxycarbonyl-2-(4-methoxyphenyl)-4-phenyl-1,3-oxazolidine-5-carboxylate are thus obtained in the form of a pale yellow solid, the characteristics of which are as follows:

$^1$H NMR spectrum (400 MHz; CDCl$_3$; δ in ppm; coupling constants J in Hz): 1.08 (s, 9H: C(CH$_3$)$_3$); 1.17 (s, 3H: CH$_3$); 1.21 (s, 3H: CH$_3$); 1.56 (s, 3H: CH$_3$); 1.60 (s 1H: OH at 1); (1.71 (s, 3H: CH$_3$); 1.91 (s, 3H: COCH$_3$); 2.08 and 2.24 (2 dd, J=16 and 9, 1H each: CH$_2$ at 14); from 2.15 to 2.30 and 2.78 (2 mts, 1H each: CH$_2$ at 6); 3.42 (s, 3H: OCH$_3$); 3.83 (s, 3H: ArOCH$_3$); 3.84 (d, J=7, 1H: H at 3); 4.12 and 4.28 (2d, J=8.5, 1H each: CH$_2$ at 20); 4.58 (d, J=5, 1H: H at 2'); 4.85 (broad d, J=10, 1H: H at 5); 5.01 (s, 1H: H at 10); 5.40 (dd, J=11 and 8, 1H: H at 7; 5.47 (mt, 1H: H at 3'); 5.65 (d, J=7, 1H: H at 2); 6.12 (broad t, J=9, 1H: H at 13); 6.42 (mt, 1H: H at 5'); 6.94 (d, J=8.5, 2H: aromatic H ortho to the OCH$_3$); from 7.20 to 7.45 (mt, 5H: aromatic H at 3'); 7.42 (d, J=8.5, 2H: aromatic H meta to the OCH$_3$); 7.50 (t, J=7.5, 2H: OCOC$_6$H$_5$ meta-H); 7.64 (t, J=7.5, 1H: OCOC$_6$H$_5$ para-H); 8.02 (d, J=7.5, 2H: OCOC$_6$H$_5$ ortho-H).

A solution of 721 mg of 4α-acetoxy-2α-benzoyloxy-5β, 20-epoxy-1β-hydroxy-10β-methoxy-9-oxo-7β-trifluoromethanesulphonyloxy-11-taxen-13α-yl (2R,4S,5R)-3-tert-butoxycarbonyl-2-(4-methoxyphenyl)-4-phenyl-1,3-oxazolidine-5-carboxylate in 13.5 cm³ of 0.1N hydrochloric ethanol solution is kept stirring for 1 hour under an argon atmosphere at a temperature in the region of 0° C., then for 4 hours at a temperature in the region of 20° C. and finally for 16 hours at a temperature in the region of 0° C. The reaction mixture is diluted with 25 cm³ of dichloromethane and washed two times with 5 cm³ distilled water. The organic phase is dried over magnesium sulphate, filtered on a sinter funnel and then concentrated to dryness under reduced pressure (0.27 kPa) at a temperature in the region of 40° C. 704 mg of a pale yellow foam are thus obtained, which product is purified by chromatography at atmospheric pressure on 70 g of silica (0.063–0.2 mm) contained in a column 2.5 cm in diameter, by elution (elution gradient: ethyl acetate/dichloromethane from 0/100 to 15/85 by volume), collecting 10 cm³ fractions. The fractions containing only the desired product are combined and concentrated to dryness under reduced pressure (0.27 kPa) at 40° C. for 2 hours. 539.5 mg of 4α-acetoxy-2α-benzoyloxy-5β,20-epoxy-1β-hydroxy-10β-methoxy-9-oxo-7β-trifluoromethanesulphonyloxy-11-taxen-13α-yl (2R,3S)-3-tert-butoxycarbonylamino-2-hydroxy-3-phenylpropionate are thus obtained in the form of an ivory foam whose characteristics are as follows:

$^1$H NMR spectrum (400 MHz; CDCl$_3$; δ in ppm; coupling constants J in Hz): 1.22 (s, 3H: CH$_3$); 1.25 (s, 3H: CH$_3$); 1.37 (s, 9H: C(CH$_3$)$_3$); 1.70 (s 1H: OH at 1); 1.88 (s, 3H: CH$_3$); 1.95 (s, 3H: CH$_3$); 2.26 and 2.82 (2 mts, 1H each: CH$_2$ at 6); 2.32 (d, J=9, 2H: CH$_2$ at 14); 2.41 (s, 3H: COCH$_3$); 3.36 (unres. mult., 1H: OH at 2'); 3.47 (s, 3H: OCH$_3$); 3.95 (d, J=7, 1H: H at 3); 4.19 and 4.35 (2 d, J=8.5, 1H each: CH$_2$ at 20); 4.63 (mt, 1H: H at 2'); 4.93 (broad d, J=10, 1H: H at 5); 5.11 (s, 1H: H at 10); 5.27 (broad d, J=10, 1H: H at 3'); 5.40 (d, J=10, 1H: CONH); 5.45 (dd, J=10.5 and 8, 1H: H at 7); 5.70 (d, J=7, 1H: H at 2); 6.26 (broad t, J=9, 1H: H at 13); from 7.25 to 7.45 (mt, 5H: aromatic H at 3'); 7.51 (t, J=7.5, 2H: OCOC$_6$H$_5$ meta-H); 7.64 (t, J=7.5, 1H: OCOC$_6$H$_5$ para-H); 8.10 (d, J=7.5, 2H: OCOC$_6$H$_5$ ortho-H).

To a solution of 265 mg of 4α-acetoxy-2α-benzoyloxy-5β,20-epoxy-1β-hydroxy-10β-methoxy-9-oxo-7β-trifluoromethanesulphonyloxy-11-taxen-13α-yl (2R,3S)-3-tert-butoxycarbonylamino-2-hydroxy-3-phenylpropionate in 3 cm³ of acetonitrile and 0.3 cm³ of tetrahydrofuran are added, at a temperature in the region of 20° C., 200 mg of powdered 4 Å molecular sieves followed by 300 mg of sodium chloride. After 5 minutes at a temperature in the region of 20° C., the suspension obtained, kept under an argon atmosphere, is maintained at reflux for 3 hours. After cooling to a temperature in the region of 20° C., the reaction mixture is filtered on a sinter funnel packed with Celite. After rinsing the sinter funnel with 30 cm³ of an ethyl acetate dichloromethane mixture (50/50 by volume) and concentration of the filtrate to dryness under reduced pressure (0.27 kPa) at a temperature in the region of 40° C., 280 mg of an ivory foam are obtained, which product is purified by thin layer preparative chromatography: 9 Merck preparative plates, Kieselgel 60F254, thickness 0.25 mm, deposited in solution in dichloromethane, eluting with a methanol/dichloromethane mixture (5–95 by volume). After elution of the zone corresponding to the main product with a methanol/dichloromethane mixture (15/85 by volume), filtration on a sinter funnel and then evaporation of the solvents under reduced pressure (0.27 kPa) at a temperature in the region of 40° C., 142.6 mg of 4α-acetoxy-2α-benzoyloxy-5β,20-epoxy-1β-hydroxy-10β-methoxy-7β,8β-methylene-9-oxo-19-nor-11-taxen-13α-yl (2R,3S)-3-tert-butoxycarbonylamino-2-hydroxy-3-phenylpropionate are obtained in the form of a white foam, the characteristics of which are as follows:

$^1$H NMR spectrum (400 MHz; CDCl$_3$; temperature of 333° K; δ in ppm; coupling constants J in Hz): 1.26 (s, 3H: CH$_3$); 1.29 (s, 3H: CH$_3$); 1.31 (s, 9H: C(CH$_3$)$_3$); 1.34 (mt, 1H: H at 7); 1.65 and 2.33 (2 mts, 1H each: CH$_2$ at 19); 1.85 (s, 1H: OH at 1); 1.88 (s, 3H: CH$_3$); 2.12 and from 2.30 to 2.45 (broad d and mt respectively, J=16, 1H each: CH$_2$ at 6); 2.24 and from 2.30 to 2.45 (dd and mt respectively, J=16 and 9, 1H each: CH$_2$ at 14); 2.39 (s, 3H: COCH$_3$); 3.33 (unres. mult., 1H: OH at 2'); 3.47 (s, 3H: OCH$_3$); 4.06 and 4.32 (2 d, J=8.5, 1H each: CH$_2$ at 20); 4.12 (d, J=7, 1H: H at 3); 4.62 (mt, 1H: H at 2'); 4.74 (d, J=4, 1H: H at 5); 4.75 (s, 1H: H at 10); 5.28 (broad d, J=10, 1H: H at 3'); 5.37 (d, J=10, 1H: CONH); 5.68 (d, J=7, 1H: H at 2); 6.32 (broad t, J=9, 1H: H at 13); from 7.25 to 7.45 (mt, 5H: aromatic H at 3'); 7.52 (t, J=7.5, 2H: OCOC$_6$H$_5$ meta-H); 7.62 (t, J=7.5, 1H: OCOC$_6$H$_5$ para-H); 8.16 (d, J=7.5, 2H: OCOC$_6$H$_5$ ortho-H).

4α-Acetoxy-2α-benzoyloxy-5β,20-epoxy-1β,13α-dihydroxy-10β-methoxy-9-oxo-7β-trifluoromethanesulphonyloxy-11-taxene may be prepared in the following way:

To a suspension of 0.5 g of 4α-acetoxy-2α-benzoyloxy-5β,20-epoxy-1β,7β,13α-trihydroxy-10β-methoxy-9-oxo-11-taxene in 10 cm$^3$ of anhydrous dichloromethane and 0.3 cm$^3$ of anhydrous pyridine, cooled to a temperature in the region of 0° C. and kept under an argon atmosphere, is added dropwise 0.31 cm$^3$ of trifluoromethanesulphonic anhydride. The reaction mixture is stirred at a temperature in the region of 20° C. for one hour and is then diluted with 20 cm$^3$ of dichloromethane and 5 cm$^3$ of distilled water. After separation of the phases by settling, the aqueous phase is reextracted two times with 5 cm$^3$ of dichloromethane. The organic phases are combined, dried over magnesium sulphate, filtered on sintered glass and concentrated to dryness under reduced pressure (0.27 kPa) at a temperature in the region of 40° C. 0.79 g of an orange solid is thus obtained, which product is purified by chromatography at atmospheric pressure on 50 g of silica (0.063–0.2 mm) contained in a column 2.5 cm in diameter (elution gradient: ethyl acetate/dichloromethane from 0/100 to 25/75 by volume), collecting 15 cm$^3$ fractions. The fractions containing only the desired product are combined and concentrated to dryness under reduced pressure (0.27 kPa) at 40° C. for 2 hours. 504 mg of 4α-acetoxy-2α-benzoyloxy-5β,20-epoxy-1β,13α-dihydroxy-10β-methoxy-9-oxo-7β-trifluoromethanesulphonyloxy-11-taxene are thus obtained in the form of a white solid, the characteristics of which are as follows:

$^1$H NMR spectrum (400 MHz; CDCl$_3$; δ in ppm; coupling constants J in Hz): 1.10 (s, 3H: CH$_3$); 1.19 (s, 3H: CH$_3$); 1.86 (s, 3H: CH$_3$); 2.09 (d, J=5, 1H: OH at 13); 2.15 (s, 3H: CH$_3$); 2.25 and 2.85 (2 mts, 1H each: CH$_2$ at 6); 2.32 (d, J=9, 2H: CH$_2$ at 14); 2.33 (s, 3H: COCH$_3$); 3.48 (s, 3H: OCH$_3$); 4.03 (d, J=7, 1H: H at 3);, 4.18 and 4.35 (2 d, J=8.5, 1H each: CH$_2$ at 20); 4.92 (mt, 1H: H at 13); 4.96 (broad d, J=10, 1H: H at 5); 5.16 (s, 1H: H at 10); 5.53 (dd, J=11 and 7, 1H: H at 7); 5.66 (d, J=7, 1H : H at 2); 7.49 (t, J=7.5, 2H: OCOC$_6$H$_5$ meta-H); 7.64 (t, J=7.5, 1H: OCOC$_6$H$_5$ para-H); 8.10 (d, J=7.5, 2H: OCOC$_6$H$_5$ ortho-H).

4α-Acetoxy-2α-benzoyloxy-5β,20-epoxy-1β,7β,13α-trihydroxy-10β-methoxy-9-oxo-11-taxene may be prepared in the following way:

To a solution of 3.62 g of 4α-acetoxy-2 α-benzoyloxy-5β,20-epoxy-1β-hydroxy-10β-methoxy-9-oxo-7β,13α-bis(triethylsiloxy)-11-taxene in 30 cm$^3$ of dichloromethane, kept under an argon atmosphere and at a temperature in the region of 0° C., are added slowly 50 cm$^3$ of hydrogen fluoride-triethylamine complex (3HF.Et$_3$N). After 48 hours at a temperature in the region of 20° C., the reaction mixture is poured onto a suspension of 100 cm$^3$ of supersaturated aqueous sodium hydrogen carbonate solution maintained at a temperature in the region of 0° C. After separation of the phases by settling, the aqueous phase is extracted two times with 80 cm$^3$ of dichloromethane and then two times with 80 cm$^3$ of ethyl acetate. The organic phases are combined, dried over magnesium sulphate, filtered on a sinter funnel and concentrated to dryness under reduced pressure (0.27 kPa) at a temperature in the region of 40° C. 3.45 g of a yellow foam are thus obtained, which product is purified by chromatography at atmospheric pressure on 150 g of silica (0.063–0.2 mm) contained in a column 3.5 cm$^3$ in diameter, eluting with a methanol/dichloromethane mixture (5/95 by volume), collecting 35 cm$^3$ fractions. The fractions containing only the desired product are combined and concentrated to dryness under reduced pressure (0.27 kPa) at 40° C. for 2 hours. 1.97 g of 4α-acetoxy-2α-benzoyloxy-5β,20-epoxy-1β,7β,13α-trihydroxy-10β-methoxy-9-oxo-11-taxene are thus obtained in the form of a white solid, the characteristics of which are as follows:

$^1$H NMR spectrum (400 MHz; CDCl$_3$; δ in ppm; coupling constants J in Hz): 1.10 (s, 3H: CH$_3$); 1.19 (s, 3H: CH$_3$); 1.48 (d, J=8.5, 1H: OH at 7); 1.70 (s, 3H: CH$_3$); 1.81 and 2.61 (2 mts, 1H each: CH$_2$ at 6); 2.09 (d, J=5, 1H: OH at 13); 2.11 (2, 3H: CH$_3$); 2.30 (s, 3H: COCH$_3$); 2.32 (d, J=9, 2H: CH$_2$ at 14); 3.48 (s, 3H: OCH$_3$); 3.97 (d, J=7, 1H: H at 3); 4.18 and 4.33 (2 d, J=8.5, 1H each: CH$_2$ at 20); 4.31 (mt, 1H: H at 7); 4.93 (mt, 1H: H at 13); 4.99 (s, 1H: H at 10); 5.01 (broad d, J=10, 1H: H at 5); 5.66 (d, J=7, 1H: H at 2); 7.49 (t, J=7.5, 2H: OCOC$_6$H$_5$ meta-H); 7.63 (t, J=7.5, 1H: OCOC$_6$H$_5$ para-H); 8.12 (d, J=7.5, 2H: OCOC$_6$H$_5$ ortho-H).

4α-Acetoxy-2α-benzoyloxy-5β,20-epoxy-1β-hydroxy-10β-methoxy-9-oxo-7β,13α-bis(triethylsiloxy)-11-taxene may be prepared in the following way:

To a solution of 5 g of 4α-acetoxy-2α-benzoyloxy-5β,20-epoxy-1β,10β-dihydroxy-9-oxo-7β,13α-bis(triethylsiloxy)-1-taxene in 25 cm$^3$ of iodomethane, kept under an argon atmosphere and at a temperature in the region of 0° C., are added portionwise 375 mg of sodium hydride at a concentration of 50% by weight in liquid petrolatum. The solution is kept stirring for 45 minutes at a temperature in the region of 0° C. and then for 5 hours 30 minutes at a temperature in the region of 20° C. The reaction mixture is again cooled to a temperature in the region of 0° C. and 125 mg of sodium hydride at a concentration of 50% by weight in liquid petrolatum are added portionwise. After 1 hour at 20° C. and then 18 hours at 5° C., the reaction mixture is diluted with 50 cm$^3$ of dichloromethane, poured onto 50 cm$^3$ of saturated aqueous ammonium chloride solution and the phases are separated by settling. The aqueous phase is reextracted two times with 30 cm$^3$ of dichloromethane and the organic phases are then combined, washed with 10 cm$^3$ of distilled water, dried over magnesium sulphate, filtered on sintered glass and concentrated to dryness under reduced pressure (0.27 kPa) at a temperature in the region of 40° C. 5.15 g of a yellow foam are thus obtained, which product is purified by chromatography at atmospheric pressure on 300 g of silica (0.063–0.2 mm) contained in a column 5 cm in diameter (elution gradient: ethyl acetate/dichloromethane from 0/100 to 10/90 by volume), eluting 30 cm$^3$ fractions. The fractions containing only the desired product are combined and concentrated to dryness under reduced pressure (0.27 kPa) at 40° C. for 2 hours. 3.62 g of 4α-acetoxy-2α-benzoyloxy-5β,20-epoxy-1β-hydroxy-10β-methoxy-9-oxo-7β,13α-bis(triethylsiloxy)-11-taxene are thus obtained in the form of a pale yellow foam, the characteristics of which are as follows:

$^1$H NMR spectrum (600 MHz; CDCl$_3$; δ in ppm; coupling constants J in Hz): 0.58 and 0.69 (2 mts, 6H each: CH$_2$ ethyl); 0.97 and 1.04 (2 t, J=7.5, 9H each: CH$_3$ ethyl); 1.15 (s, 3H: CH$_3$); 1.18 (s, 3H: CH$_3$); 1.58 (s, 1H: OH at 1); 1.68 (s, 3H: CH$_3$); 1.89 and 2.48 (2 mts, 1H each: CH$_2$ at 6); 2.04 (s, 3H: CH$_3$); 2.15 and 2.23 (2 dd, J=16 and 9, 1H each: CH$_2$ at 14); 2.29 (s, 3H: COCH$_3$); 3.40 (s, 3H: OCH$_3$); 3.83 (d, J=7, 1H: H at 3); 4.15 and 4.30 (2 d, J=8.5, 1H each: CH$_2$ at 20); 4.43 (dd, J=11 and 7, 1H: H at 7); 4.91 (s, 1H: H at 10); 4.96 (broad d, J=10, 1H: H at 5); 5.01 (broad t, J=9, 1H: H at 13); 5.62 (d, J=7, 1H: H at 2); 7.46 (t, J=7.5, 2H: OCOC$_6$H$_5$ meta-H); 7.60 (t, J=7.5, 1H: OCOC$_6$H$_5$ para-H); 8.09 (d, J=7.5, 2H: OCOC$_6$H$_5$ ortho-H).

4α-Acetoxy-2α-benzoyloxy-5β,20-epoxy-1β,10β-dihydroxy-9-oxo-7β,13α-bis(triethylsilyloxy)-11-taxene may be prepared in the following way:

To a solution of 14 g of 4α-acetoxy-2α-benzoyloxy-5β,20-epoxy-1β,7β,10β,13α-tetrahydroxy-9-oxo-11-taxene in 50 cm$^3$ of anhydrous pyridine, kept under an argon atmosphere and at a temperature in the region of 20° C., are added 10.8 cm$^3$ of triethylsilyl chloride. After 17 hours at a temperature in the region of 20° C., the reaction mixture is brought to a temperature in the region of 115° C. and 10.8 cm$^3$ of triethylsilyl chloride are then added. After 3 hours 15 minutes at a temperature in the region of 115° C., the reaction mixture is cooled to a temperature in the region of 20° C. and diluted with 300 cm$^3$ of ethyl acetate and 100 cm$^3$ of distilled water. After separation of the phases by settling, the aqueous phase is reextracted two times with 50 cm$^3$ of ethyl acetate. The organic phases are combined, washed with 50 cm$^3$ of saturated aqueous sodium chloride solution, dried over magnesium sulphate, filtered on a sinter funnel and then concentrated to dryness under reduced pressure (0.27 kPa) at a temperature in the region of 40° C. 63.1 g of a brown oil are thus obtained, which product is purified by chromatography at atmospheric pressure on 800 g of silica (0.063–0.2 mm) contained in a column 7 cm in diameter (elution gradient: ethyl acetate/dichloromethane from 0/100 to 5/95 by volume), collecting 60 cm$^3$ fractions. The fractions containing only the desired product are combined and concentrated to dryness under reduced pressure (0.27 kPa) at 40° C. for 2 hours. 9.77 g of 4α-acetoxy-2α-benzoyloxy-5β,20-epoxy-1β,10β-dihydroxy-9-oxo-7β,13α-bis(triethylsiloxy)-11-taxene are thus obtained in the form of a cream-colored foam, the characteristics of which are as follows:

$^1$H NMR spectrum (400 MHz; CDCl$_3$; δ in ppm; coupling constants J in Hz): 0.55 and 0.68 (2 mts, 6H each: CH$_2$ ethyl); 0.94 and 1.03 (2 t, J=7.5, 9H each: CH$_3$ ethyl); 1.08 (s, 3H: CH$_3$); 1.17 (s, 3H: CH$_3$); 1.58 (s, 1H: OH at 1); 1.73 (s, 3H: CH$_3$); 1.91 and 2.57 (2 mts, 1H each: CH$_2$ at 6); 2.04 (s, 3H: CH$_3$); 2.12 and 2.23 (2 dd, J=16 and 9, 1H each: CH$_2$ at 14); 2.30 (s, 3H: COCH$_3$); 3.88 (d, J=7, 1H: H at 3); 4.16 and 4.32 (2 d, J=8.5, 1H each: CH$_2$ at 20); 4,27 (d, J=1, 1H: OH at 10); 4.40 (dd, J=11 and 7, 1H: H at 7); 4.95 (broad d, J=10 1H: H at 5); 4.95 (mt, 1H: H at 13); 5.16 (d, J=1, 1H: H at 10); 5.60 (d, J=7, 1H: H at 2); 7.46 (t, J=7.5, 2H: OCOC$_6$H$_5$ meta-H); 7.60 (t, J=7.5, 1H: OCOC$_6$H$_5$ para-H); 8.09 (d, J=7.5, 2H: OCOC$_6$H$_5$ ortho-H).

EXAMPLE 2

To a solution of 250 mg of 4α-acetoxy-2α-benzoyloxy-5β,20-epoxy-1β-hydroxy-10β-ethoxy-9-oxo-7β-trifluoromethanesulphonyloxy-11-taxen-13α-yl (2R,3S)-3-tert-butoxycarbonylamino-2-hydroxy-3-phenylpropionate in 2.5 cm$^3$ of acetonitrile and 0.25 cm$^3$ of tetrahydrofuran are added, at a temperature in the region of 20° C., 100 mg of powdered 4 Å molecular sieves followed by 200 mg of sodium chloride. After 10 minutes at a temperature in the region of 20° C., the solution obtained, kept under an argon atmosphere, is maintained at reflux for 2 hours. After cooling to a temperature in the region of 20° C. the reaction mixture is diluted with 50 cm$^3$ of ethyl acetate and filtered on a sinter funnel packed with Celite. After rinsing the sinter funnel with 10 cm$^3$ of ethyl acetate, washing the filtrate two times with 10 cm$^3$ of saturated aqueous sodium hydrogen carbonate solution, two times with 10 cm$^3$ of distilled water and two times with 10 cm$^3$ of saturated aqueous sodium chloride solution, drying over magnesium sulphate, filtration on a sinter funnel and concentration of the filtrate to dryness under reduced pressure (2.7 kPa) at a temperature in the region of 40° C., 209 mg of a yellow foam are obtained, which product is purified by thin layer preparative chromatography: 9 Merck preparative plates, Kieselgel 60F254, thickness 0.5 mm, applied as a solution in dichloromethane, eluting with a methanol/dichloromethane mixture (5/95 by volume). After elution of the zone corresponding to the main product with a methanol/dichloromethane mixture (15/85 by volume), filtration on a sinter funnel and then evaporation of the solvents under reduced pressure (2.7 kPa) at a temperature in the region of 40° C., 66.5 mg of 4α-acetoxy-2α-benzoyloxy-5β,20-epoxy-1β-hydroxy-10β-ethoxy-7β,8β-methylene-9-oxo-19-nor-11-taxen-13α-yl (2R,3S)-3-tert-butoxycarbonylamino-2-hydroxy-3-phenylpropionate are obtained in the form of an ivory foam, the characteristics of which are as follows:

$^1$H NMR spectrum (300 MHz; CDCl$_3$; chemical shifts δ in ppm; coupling constants J in Hz): 1.25 (s, 3H: CH$_3$); 1.33 (t, J=7, 3H: CH$_3$ of the ethyl); 1.34 (s, 9H: C(CH$_3$)$_3$); 1.35 (s, 3H: CH$_3$); 1.37 (mt, 1H: H at 7); from 1.55 to 1.70 and from 2.20 to 2.40 (2 mts, 1H each: CH$_2$ at 19); 1.80 (s, 1H: OH at 1); 1.85 (s, 3H: CH$_3$); 2.10 and 2.40 (broad d and dt respectively, J=15 and J=15 and 4, 1H each: CH$_2$ at 6); 2.20 and the 2.20 to 2.40 (dd and mt respectively, J=16 and 9, 1H each: CH$_2$ at 14); 2.38 (s, 3H: COCH$_3$); 3.30 (mt, 1H: OH at 2'); 3.60 (limiting AB, 2H: OCH$_2$ of the ethyl); 4.05 and 4.30 (2 d, J=8.5, 1H each: CH$_2$ at 20); 4.13 (d, J=7.5, 1H: H at 3); 4.62 (mt, 1H: H at 2'); 4.74 (broad d, J=4, 1H: H at 5); 4.83 (s, 1H: H at 10); 5.27 (broad d, J=10, 1H: H at 3'); 5.35 (d, J=10, 1H: CONH); 5.67 (d, J=7.5, 1H: H at 2); 6.30 (broad t, J=9, 1H: H at 13); from 7.25 to 7.45 (mt, 5H: aromatic H at 3'); 7.52 (t, J=7.5, 2H: OCOC$_6$H$_5$ meta-H); 7.63 (t, J=7.5, 1H: OCOC$_6$H$_5$ para-H); 8.15 (d, J=7.5, 2H: OCOC$_6$H$_5$ ortho-H).

4α-Acetoxy-2α-benzoyloxy-5β,20-epoxy-1β-hydroxy-10β-ethoxy-9-oxo-7β-trifluoromethanesulphonyloxy-11-taxen-13α-yl (2R,3S)-3-tert-butoxycarbonylamino-2-hydroxy-3-phenylpropionate may be prepared in the following way:

A solution of 423 mg of 4α-acetoxy-2α-benzoyloxy-5β,20-epoxy-1β-hydroxy-10β-ethoxy-9-oxo-7β-trifluoromethanesulphonyloxy-11-taxen-13α-yl (2R,4S,5R)-3-tert-butoxycarbonyl-2-(4-methoxyphenyl)-4-phenyl-1,3-oxazolidine-5-carboxylate in 7 cm$^3$ of 0.1N hydrochloric ethanol is kept under an argon atmosphere at a temperature in the region of 0° C. for 15 hours. The reaction mixture is diluted with 35 cm$^3$ of dichloromethane and washed two times with 7 cm$^3$ of distilled water and then 7 cm$^3$ of saturated aqueous sodium chloride solution. The organic phase is dried over magnesium sulphate, filtered on a sinter funnel and then concentrated to dryness under reduced pressure (2.7 kPa) at a temperature in the region of 40° C. 358 mg of a brown solid are thus obtained, which product is purified by chromatography at atmospheric pressure on 30 g of silica (0.063–0.2 mm) contained in a column 2.5 cm in diameter, by elution (elution gradient: methanol/dichloromethane from 1/99 to 5/95 by volume), collecting 10 cm$^3$ fractions. The fractions containing only the desired product are combined and concentrated to dryness under reduced pressure (2.7 kPa) at 40° C. for 2 hours. 263.1 mg of 4α-acetoxy-2α-benzoyloxy-5β,20-epoxy-1β-hydroxy-10β-ethoxy-9-oxo-7β-trifluoromethanesulphonyloxy-11-taxen-13α-yl (2R,3S)-3-tert-butoxycarbonylamino-2-hydroxy-3-phenylpropionate are thus obtained in the form of a cream-colored foam, the characteristics of which are as follows:

$^1$H NMR spectrum (300 MHz; CDCl$_3$; chemical shifts δ in ppm; coupling constants J in Hz): 1.25 (s, 3H: CH$_3$); 1.26 (s, 3H: CH$_3$), 1.27 (t, J=7, 3H: CH$_3$ of the ethyl); 1.37 (s, 9H: C(CH$_3$)$_3$); 1.66 (s, 1H: OH at 1); 1.85 (s, 3H: CH$_3$); 1.95 (s, 3H: CH$_3$); 2.25 and 2.80 (2 mts, 1H each: CH$_2$ at 6); 2.30 (d, J=9, 2H: CH$_2$ at 14); 2.40 (s, 3H: COCH$_3$); 3.35 (d, J=4, 1H: OH at 2'); 3.55 and 3.65 (2 mts, 1H each: OCH$_2$ of the ethyl); 3.95 (d, J=7.5, Hz, 1H: H at 3); 4.17 and 4.35 (2 d, J=8.5, 1H each: CH$_2$ at 20); 4.62 (mt, 1H: H at 2'); 4.93 (broad d, J=10, 1H: H at 5); 5.17 (s, 1H: H at 10); 5.27 (broad d, J=10, 1H: H at 3'); 5.37 (d, J=10, 1H: CONH); 5.45 (dd, J=11 and 6.5, 1H: H at 7); 5.73 (d, J=7.5, 1H: H at 2); 6.25 (broad t, J=9, 1H: H at 13); from 7.25 to 7.45 (mt, 5H; aromatic H at 3'); 7.52 (t, J=7.5, 2H: OCOC$_6$H$_5$ meta-H); 7.63 (t, J=7.5, 1H: OCOC$_6$H$_5$ para-H); 8.10 (d, J=7.5, 2H: OCOC$_6$H$_5$ ortho-H).

4α-Acetoxy-2α-benzoyloxy-5β,20-epoxy-1β-hydroxy-10β-ethoxy-9-oxo-7β-trifluoromethanesulphonyloxy-11-taxen-13α-yl (2R,4S,5R)-3-tert-butoxycarbonyl-2-(4-methoxyphenyl)-4-phenyl-1,3-oxazolidine-5-carboxylate may be prepared in the following way:

To a suspension of 238 mg of 4α-acetoxy-2α-benzoyloxy-5β,20-epoxy-1β,13α-dihydroxy-10β-ethoxy-9-oxo-7β-trifluoromethanesulphonyloxy-11-taxene and 182 mg of (2R,4S,5R)-3-tert-butoxycarbonyl-2-(4-methoxyphenyl)-4-phenyl-1,3-oxazolidine-5-carboxylic acid in 2 cm$^3$ of anhydrous toluene and 0.2 cm$^3$ of dichloromethane are successively added, at a temperature-in the region-of 20° C., 116 mg of dicyclohexylcarbodiimide and 13 mg of 4-N,N'-dimethylaminopyridine. After 45 minutes at a temperature in the region of 20° C., the reaction mixture is purified (applied directly to the column) by chromatography at atmospheric pressure on 50 g of silica (0.063–0.2 mm) contained in a column 2.5 cm in diameter, eluting with a methanol/dichloromethane mixture (1/99 by volume), collecting 10 cm$^3$ fractions. The fractions containing only the desired product are combined and concentrated to dryness under reduced pressure (0.27 kPa) at 40° C. for 2 hours. 443.6 mg of 4α-acetoxy-2α-benzoyloxy-5β,20-epoxy-1β-hydroxy-10 β-ethoxy-9-oxo-7β-trifluoromethanesulphonyloxy-11-taxen-13α-yl (2R,4S,5R)-3-tert-butoxycarbonyl-2-(4-methoxyphenyl)-4-phenyl-1,3-oxazolidine-5-carboxylate are thus obtained in the form of a pale yellow foam.

4α-Acetoxy-2α-benzoyloxy-5β,20-epoxy-1β,13α-dihydroxy-10β-ethoxy-9-oxo-7β-trifluoromethanesulphonyloxy-11-taxene may be prepared in the following way:

To a suspension of 199 mg of 4α-acetoxy-2α-benzoyloxy-5β,20-epoxy-1β,7β,13α-trihydroxy-10β-ethoxy-9-oxo-11-taxene in 2 cm$^3$ of anhydrous dichloromethane and 0.14 cm$^3$ of anhydrous pyridine, cooled to a temperature in the region of 0° C. and kept under an argon atmosphere, is added dropwise 0.145 cm$^3$ of iS trifluoromethanesulphonic anhydride. The reaction mixture is stirred at a temperature in the region of 0° C. for one hour and 0.07 cm$^3$ of trifluoromethanesulphonic anhydride is then added dropwise. The reaction mixture is stirred at a temperature in the region of 0° C. for 1.5 hours, diluted with 1 cm$^3$ of a methanol/dichloromethane mixture (5/95 by volume) and concentrated to dryness under reduced pressure (2.7 kPa) at a temperature in the region of 30° C. The crude residue obtained is purified by chromatography at atmospheric pressure on 30 g of silica (0.063–0.2 mm) contained in a column 2.5 cm in diameter, eluting with a methanol/dichloromethane mixture (2/98 by volume), collecting 10 cm$^3$ fractions. The fractions containing only the desired product are combined and concentrated to dryness under reduced pressure (2.7 kPa) at 40° C. for 2 hours. 238.2 mg of 4α-acetoxy-2α-benzoyloxy-5β,20-epoxy-1β,13α-dihydroxy-10β-ethoxy-9-oxo-7β-trifluoromethanesulphonyloxy-11-taxene are thus obtained in the form of a yellow foam.

4α-Acetoxy-2α-benzoyloxy-5β,20-epoxy-1β,7β,13α-trihydroxy-10β-ethoxy-9-oxo-11-taxene (or 10β-ethoxy-10-deacetoxybaccatin III) may be prepared in the following way:

To a solution of 591 mg of 4α-acetoxy-2α-benzoyloxy-5β,20-epoxy-1β-hydroxy-10β-ethoxy-9-oxo-7β,13α-bis(triethylsilyloxy)-11-taxene in 6 cm$^3$ of dichloromethane, kept under an argon atmosphere and at a temperature in the region of 20° C., are added 9 cm$^3$ of hydrogen fluoride-triethylamine complex (3HF.Et$_3$N). After 21 hours at a temperature in the region of 20° C., the reaction mixture is diluted with 40 cm$^3$ of dichloromethane and poured onto a suspension of 40 cm$^3$ of supersaturated aqueous NaHCO$_3$ solution, kept at a temperature in the region of 0° C. After dilution with 10 cm$^3$ of distilled water and separation of the phases by settling, the aqueous phase is reextracted two times with 20 cm$^3$ of diethyl ether. The organic phases are combined, washed with 20 cm$^3$ of distilled water, 20 cm$^3$ of saturated aqueous sodium chloride solution, dried over magnesium sulphate, filtered on a sinter funnel and concentrated to dryness under reduced pressure (2.7 kPa) at a temperature in the region of 40° C. 370 mg of a pale yellow foam are thus obtained, which product is purified by chromatography at atmospheric pressure on 35 g of silicone (0.063–0.2 mm) contained in a column 2.5 cm in diameter, eluting with a methanol/dichloromethane mixture (2/98 by volume), collecting 15 cm$^3$ fractions. The fractions containing only the desired products are combined and concentrated to dryness under reduced pressure (2.7 kPa) at 40° C. for 2 hours. 236.2 mg of 4α-acetoxy-2α-benzoyloxy-5β,20-epoxy-1β,7β,13α-trihydroxy-10β-ethoxy-9-oxo-11-taxene are thus obtained in the form of a white solid, the characteristics of which are as follows:

$^1$H NMR spectrum (400 MHz; CDCl$_3$; chemical shifts δ in ppm; coupling constants J in Hz): 1.08 (s, 3H: CH$_3$); 1.19 (s, 3H: CH$_3$), 1.29 (t, J=7.5, 3H: CH$_3$ of the ethyl); 1.38 (d, J=9, 1H: OH at 7); 1.59 (s, 1H: OH at 1); 1.69 (s, 3H: CH$_3$); 1.82 and 2.62 (2 mts, 1H each: CH$_2$ at 6); 2.02 (d, J=5, 1H: OH at 13); 2.08 (s, 3H: CH$_3$); 2.30 (s, 3H: COCH$_3$); 2.32 (d, J=9, 2H: CH$_2$ at 14); 3.56 and 3.67 (2mts, 1H each: OCH$_2$ of the ethyl); 3.98 (d, J=7, 1H: H at 3); 4.18 and 4.33 (2 d, J=8.5, 1H each: CH$_2$ at 20); 4.30 (mt, 1H: H at 7); 4.90 (mt, 1H: H at 13); 4.99 (dd, J=10 and 1.5, 1H: H at 5); 5.05 (s, 1H: H at 10); 5.66 (d, J=7, 1H: H at 2); 7.49 (t, J=7.5, 2H:

OCOC$_6$H$_5$ meta-H); 7.63 (t, J=7.5, 1H: OCOC$_6$H$_5$ para-H); 8.12 (d, J=7.5, 2H: OCOC$_6$H$_5$ ortho-H).

4α-Acetoxy-2α-benzoyloxy-5β,20-epoxy-1βhydroxy-10β-ethoxy-9-oxo-7β,13α-bis(triethylsilyloxy)-11-taxene (or 10β-ethoxy-10-deacetoxy-7,13-bis(triethylsilyl)baccatin III) may be prepared in the following way:

To a solution of 1 g of 4α-acetoxy-2α-benzoyloxy-5β, 20-epoxy-1β,10β-dihydroxy-9-oxo-7β,13α-bis (triethylsilyloxy)-11-taxene in 3 cm$^3$ of iodoethane and 4 cm$^3$ of dimethylformamide, kept under an argon atmosphere and at a temperature in the region of 20° C., are added portionwise 93 mg of sodium hydride at a concentration of 50% by weight in liquid petrolatum. The solution is kept stirring for 17 hours at a temperature in the region of 20° C. and 93 mg of sodium hydride at a concentration of 50% by weight in liquid petrolatum are then added portionwise. After 50 minutes at a temperature in the region of 20° C., the reaction mixture is diluted with 100 cm$^3$ of ethyl acetate and 10 cm$^3$ of saturated aqueous ammonium chloride solution. The organic phase, separated out by settling, is washed six times with 10 cm$^3$ of distilled water and then with 10 cm$^3$ of saturated aqueous sodium chloride solution, dried over magnesium sulphate, filtered on a sinter funnel and concentrated to dryness under reduced pressure (2.7 kPa) at a temperature in the region of 40° C. 1.2 g of a yellow foam are thus obtained, which product is purified by chromatography at atmospheric pressure on 150 g of silica (0.063–0.2 mm) contained in a column 3.5 cm in diameter, eluting with an ethyl acetate/dichloromethane mixture (2/98 and then 5/95 by volume), collecting 15 cm$^3$ fractions. The fractions containing only the desired products are combined and concentrated to dryness under reduced pressure (0.27 kPa) at 40° C. for 2 hours. 379.2 mg of 4α-acetoxy-2α-benzoyloxy-5β,20-epoxy-1β,10β-dihydroxy-9-oxo-7β,13α-bis (triethylsilyloxy)-11-taxene in the form of a pale yellow foam and 430 mg of 4α-acetoxy-2α-benzoyloxy-5β,20-epoxy-1β-hydroxy,7β,13α-bis(triethysilyoxy)-10β-ethoxy-9-oxo-11-taxene in the form of a white foam are obtained, the characteristics of which are as follows:

$^1$H NMR spectrum (400 MHz; CDCl$_3$; chemical shifts δ in ppm; coupling constants J in Hz): 0.57 and 0.70 (2 mts, 6H each: CH$_2$ of the ethyl); 0.97 and 1.03 (2 t, J=7.5, 9H each: CH$_3$ of the ethyl); 1.13 (s, 3H: CH$_3$); 1.20 (s, 3H: CH$_3$), 1.29 (t, J=7.5, 3H: CH$_3$ of the ethoxy at 10); 1.58 (s, 1H: OH at 1); 1.66 (s, 3H: CH$_3$); 1.89 and 2.58 (2 mts, 1H each: CH$_2$ at 6); 2.03 (s, 3H: CH$_3$); 2.13 and 2.23 (2 dd J=16 and 9, 1H each: CH$_2$ at 14); 2.30 (s, 3H: COCH$_3$); 3.53 (mt, 2H: CH$_2$ of the ethoxy at 10); 3.84 (d, J=7 Hz, 1H: H at 3); 4.15 and 4.30 (2 d, J=8.5, 1H each: CH$_2$ at 20); 4.43 (dd, J=11 and 6.5, 1H: H at 7): from 4.90 to 5.00 (mt, 2H: H at 13 and H at 5); 5.01 (s, 1H: H at 10); 5.21 (d, J=7, 1H: H at 2); 7.48 (t, J=7.5, 2H: OCOC$_6$H$_5$ meta-H); 7.61 (t, J=7.5, 1H: OCOC$_6$H$_5$ para-H); 8.10 (d, J=7.5, 2H: OCOC$_6$H$_5$ ortho-H).

EXAMPLE 3

To a solution of 80 mg of 4α-acetoxy-2α-benzoyloxy-5β, 20-epoxy-1β-hydroxy-10β-(1-propyl)oxy-9-oxo-7β-trifluoromethanesulphonyloxy-11-taxen-13α-yl (2R,3S)-3-tert-butoxycarbonylamino-2-hydroxy-3-phenylpropionate in 0.8 cm$^3$ of acetonitrile and 0.8 cm$^3$ of tetrahydrofuran are added, at a temperature in the region of 20° C., 50 mg of powdered 4 Å molecular sieves and then 80 mg of sodium chloride. After 5 minutes at a temperature in the region of 20° C., the solution obtained, kept under an argon atmosphere, is maintained at reflux for 2.5 hours. After cooling to a temperature in the region of 20° C., the reaction mixture is filtered over Celite. After rinsing the Celite with 5 cm$^3$ of ethyl acetate and concentration of the filtrate to dryness under reduced pressure (2.7 kPa) at a temperature in the region of 40° C., 81.2 mg of a yellow foam are obtained, which product is purified by thin layer preparative chromatography: 5 Merck preparative plates, Kieselgel 60F254, thickness 0.5 mm, applied in solution in dichloromethane, eluting with a methanol/dichloromethane mixture (5/95 by volume). After elution of the zone corresponding to the main product with a methanol/dichloromethane mixture (15/85 by volume), filtration on a sinter funnel and then evaporation of the solvents under reduced pressure (2.7 kPa) at a temperature in the region of 40° C., 36.5 mg of 4α-acetoxy-2α-benzoyloxy-5β,20-epoxy-1β-hydroxy- 10β-(1-propyl)oxy-7β,8β-methylene-9-oxo-19-nor-11-taxen-13α-yl (2R,3S)-3-tert-butoxycarbonylamino-2-hydroxy-3-phenylpropionate are obtained in the form of an ivory foam, the characteristics of which are as follows:

$^1$H NMR spectrum (300 MHz; CDCl$_3$; chemical shifts δ in ppm; coupling constants J in Hz): 0.98 (t, J=7.3H: CH$_3$ of the propyl); 1.23 (s, 3H: CH$_3$); 1.33 (s, 3H: CH$_3$); 1.33 (s, 9H: C(CH$_3$)$_3$); 1.35 (mt, 1H: H at 7); from 1.55 to 1.80 and from 2.20 to 2.40 (2 mts, 1H each: CH$_2$ at 19); from 1.55 to 1.80 (mt, 2H: CH$_2$ of the central propyl); 1.82 (s, 1H: OH at 1); 1.89 (s, 3H: CH$_3$); 2.12 and 2.40 (broad d and dt respectively, J=15 and 4, 1H each: CH$_2$ at 6); 2.22 and from 2.20 to 2.40 (dd and mt respectively, J=16 and 9, 1H each: CH$_2$ at 14); 2.40 (s, 3H: COCH$_3$); 3.30 (unres. mult., 1H: OH at 2'); 3.42 and 3.55 (2 mts, 1H each: OCH$_2$ of the propyl); 4.04 and 4.32 (2 d, J=8.5, 1H each: CH$_2$ at 20); 4.12 (d, J=7.5, 1H: H at 3); 4.62 (mt, 1H: H at 2'); 4.73 (broad d, J=4, 1H: H at 5); 4.80 (s, 1H: H at 10); 5.30 (broad d, J=10, 1H: H at 3'); 5.37 (d, J=10, 1H: CONH); 5.68 (d, J=7.5, 1H: H at 2); 6.32 (broad t, J=9, 1H: H at 13); from 7.25 to 7.45 (mt, 5H: aromatic H at 3'); 7.52 (t, J=7.5, 2H: OCOC$_6$H$_5$ meta-H); 7.62 (t, J=7.5, 1H: OCOC$_6$H$_5$ para-H); 8.12 (d, J=7.5, 2H: OCOC$_6$H$_5$ ortho-H).

4α-Acetoxy-2α-benzoyloxy-5β,20-epoxy-1β-hydroxy-10β-(1-propyl)oxy-9-oxo-7β-trifluoromethanesulphonyloxy-11-taxen-13α-yl (2R,3S)-3-tert-butoxycarbonylamino-2-hydroxy-3-phenylpropionate may be prepared in the following way:

A solution of 340 mg of 4α-acetoxy-2α-benzoyloxy-5β, 20-epoxy-1β-hydroxy-10β-(1-propyl)oxy-9-oxo-7β-trifluoromethanesulphonyloxy-11-taxen-13α-yl (2R,4S, 5R)-3-tert-butoxycarbonyl-2-(4-methoxyphenyl)-4-phenyl-1,3-oxazolidine-5-carboxylate in 4.6 cm$^3$ of 0.1N hydrochloric ethanol solution is kept under an argon atmosphere at a temperature in the region of 0° C. for 93 hours. The reaction mixture is diluted with 50 cm$^3$ of ethyl acetate and washed with 6 cm$^3$ of saturated aqueous sodium hydrogen carbonate solution, 6 cm$^3$ of distilled water and then 6 cm$^3$ of saturated aqueous sodium chloride solution. The organic phase is dried over magnesium sulphate, filtered on a sinter funnel and then concentrated to dryness under reduced pressure (2.7 kPa) at a temperature in the region of 40° C. 348 mg of a yellow resin are thus obtained, which product is purified by thin layer preparative chromatography: 6 Merck preparative plates, Kieselgel 60F254, thickness 1 mm, applied in solution in dichloromethane, eluting twice with a methanol/dichloromethane mixture (3/97 by volume). After elution of the zone corresponding to the main product with a methanol/dichloromethane mixture (15/85 by volume), filtration on a sinter funnel and then evaporation of the solvents under reduced pressure (2.7 kPa) at 40° C. for 2 hours. 61.4 mg of 4α-acetoxy-2α-benzoyloxy-5β,20- epoxy-1β-hydroxy-10β-(1-propyl)oxy-9-oxo-7β-trifluoromethanesulphonyloxy-11-taxen-13α-yl (2R,3S)-3-tert-butoxycarbonylamino-2-hydroxy-3-phenylpropionate are thus obtained in the form of a yellow foam, the characteristics of which are as follows:

$^1$H NMR spectrum (400 MHz; CDCl$_3$; chemical shifts δ in ppm; coupling constants J in Hz): 0.99 (t, J=7.3H: CH$_3$ of the propyl); 1.24 (s, 3H: CH$_3$); 1.26 (s, 3H: CH$_3$); 1.39 (s, 9H: C(CH$_3$)$_3$); 1.64 (s, 1H: OH at 1); 1.69 (mt, 2H: central CH$_2$ of the propyl); 1.87 (s, 3H: CH$_3$); 1.94 (s, 3H: CH$_3$); 2.26 and 2.83 (2 mts, 1H each: CH$_2$ at 6); 2.32 (d, J=9, 2H: CH$_2$ at 14); 2.40 (s, 3H: COCH$_3$); 3.33 (d, J=4, 1H: OH at 2'); 3.44 and 3.59 (2 mts, 1H each: OCH$_2$ of the propyl); 3.97 (d, J=7.5, 1H: H at 3); 4.19 and 4.35 (2 d, J=8.5, 1H each: CH$_2$ at 20); 4.64 (mt, 1H: H at 2'); 4.93 (broad d, J=10, 1H: H at 5); 5.17 (s, 1H: H at 10); 5.27 (broad d, J=10, 1H: H at 3'); 5.39 (d, J=10, 1H: CONH); 5.46 (dd, J=11 and 6.5, 1H: H at 7); 5.72 (d, J=7.5, 1H: H at 2); 6.25 (broad t, J=9, 1H: H at 13); from 7.25 to 7.45 (mt, 5H: aromatic H at 3'); 7.52 (t, J=7.5, 2H: OCOC$_6$H$_5$ meta-H); 7.63 (t, J=7.5, 1H: OCOC$_6$H$_5$ para-H); 8.12 (d, J=7.5, 2H: OCOC$_6$H$_5$ ortho-H).

4α-Acetoxy-2α-benzoyloxy-5β,20-epoxy-1β-hydroxy-10β-(1-propyl)oxy-9-oxo-7β-trifluoromethanesulphonyloxy-11-taxen-13α-yl (2R,4S,5R)-3-tert-butoxycarbonyl-2-(4-methoxyphenyl)-4-phenyl-1,3-oxazolidine-5-carboxylate may be prepared in the following way:

To a suspension of 204 mg of 4α-acetoxy-2α-benzoyloxy-5β,20-epoxy-1β,13α-dihydroxy-10β-(1-propyl)oxy-9-oxo-7β-trifluoromethanesulphonyloxy-11-taxene and 177 mg of (2R,4S,5R)-3-tert-butoxycarbonyl-2-(4-methoxyphenyl)-4-phenyl-1,3-oxazolidine-5-carboxylic acid in 2 cm$^3$ of dichloromethane are added successively, at a temperature in the region of 20° C., 90 mg of (2R,4S,5R)-3-tert-butoxycarbonyl-2-(4-methoxyphenyl)-4-phenyl-1,3-oxazolidine-5-carboxylic acid, 60 mg of dicyclohexylcarbodiimide and 6.2 mg of 4-N,N'-dimethylaminopyridine. After 65 hours at a temperature in the region of 20° C., 113 mg of dicyclohexylcarbodiimide and 12.5 mg of 4-N,N'-dimethylaminopyridine are added successively, at a temperature in the region of 20° C. After 2 hours at a temperature in the region of 20° C., the reaction mixture is purified (applied directly to the column) by chromatography at atmospheric pressure on 20 g of silica (0.063–0.2 mm) contained in a column 2 cm in diameter, eluting with a methanol/dichloromethane mixture (4/96 by volume), collecting 10 cm$^3$ fractions. The fractions containing only the desired product are combined and concentrated to dryness under reduced pressure (0.27 kPa) at 40° C. for 2 hours. 384 mg of a yellow solid are thus obtained, which product is purified by thin layer preparative chromatography: 6 Merck preparative plates, Kieselgel 60F254, thickness 2 mm, applied in solution in dichloromethane, eluting twice with a methanol/dichloromethane mixture (3/97 by volume). After elution of the zone corresponding to the main product with a methanol/dichloromethane mixture (15/85 by volume), filtration on a sinter funnel and then evaporation of the solvents under reduced pressure (2.7 kPa) at 40° C. for 2 hours, 323.2 mg of 4α-acetoxy-2α-benzoyloxy-5β,20-epoxy-1β-hydroxy-10β-(1-propyl)oxy-9-oxo-7β-trifluoromethanesulphonyloxy-11-taxen-13α-yl (2R,4S,5R)-3-tert-butoxycarbonyl-2-(4-methoxyphenyl)-4-phenyl-1,3-oxazolidine-5-carboxylate are thus obtained in the form of a yellow foam, the characteristics of which are as follows:

$^1$H NMR spectrum (300 MHz; CDCl$_3$; chemical shifts δ in ppm; coupling constants J in Hz): 0.96 (t, J=7, 3H: CH$_3$ of the propyl); 1.08 (s, 9H: C(CH$_3$)$_3$); 1.19 (s, 6H: CH$_3$); 1.50 (s, 1H: OH at 1); 1.58 (s, 3H: CH$_3$); 1.65 (mt, 2H: central CH$_2$ of the propyl); 1.80 (s, 3H: CH$_3$); 1.88 (unres. mult., 3H: COCH$_3$); 2.04 and 2.12 (2 dd, J=16 and 9, 1H each: CH$_2$ at 14); from 2.10 to 2.30 and 2.75 (2 mts, 1H each: CH$_2$ at 6); 3.35 and 3.50 (2 mts, 1H each: OCH$_2$ of the propyl); 3.81 (s, 3H: ArOCH$_3$); 3.82 (d, J=7.5, 1H: H at 3); 4.10 and 4.28 (2 d, J=8.5, 1H each: CH$_2$ at 20); 4.57 (d, J=4.5, 1H at 2'); 4.80 (broad d, J=10, 1H: H at 5); 5.04 (s, 1H: H at 10); 5.38 (dd, J=10.5 and 7, 1H: H at 7); 5.45 (unres. mult., 1H: H 3'); 5.62 (d, J=7.5, 1H: H at 2); 6.08 (broad t, J=9, 1H: H at 13); 6.40 (broad unres. mult., 1H: H at 5'); 6.92 (d, J=8.5, 2H: aromatic H ortho to the OCH$_3$); from 7.30 to 7.60 (mt, 7H: aromatic H at 3'and aromatic H meta to the OCH$_3$); 7.50 (t, J=7.5, 2H: OCOC$_6$H$_5$ meta-H); 7.62 (t, J=7.5, 1H: OCOC$_6$H$_5$ para-H); 8.02 (d, J=7.5, 2H: OCOC$_6$H$_5$ ortho-H).

4α-Acetoxy-2α-benzoyloxy-5β,20-epoxy-1β,13α-dihydroxy-10β-(1-propyl)oxy-9-oxo-7β-trifluoromethanesulphonyloxy-11-taxene may be prepared in the following way:

To a suspension of 200 mg of 4α-acetoxy-2α-benzoyloxy-5β,20-epoxy-1β,7β,13α-trihydroxy-10β-(1-propyl)oxy-9-oxo-11-taxene in 2 cm$^3$ of anhydrous dichloromethane and 0.14 cm$^3$ of anhydrous pyridine, cooled to a temperature in the region of 0° C. and kept under an argon atmosphere, is added dropwise 0.145 cm$^3$ of trifluoromethanesulphonic anhydride. The reaction mixture is stirred at a temperature in the region of 0° C. for 55 minutes and then diluted with 2 cm$^3$ of a methanol/dichloromethane mixture (10/90 by volume) and concentrated to dryness under reduced pressure (2.7 kPa) at a temperature in the region of 30° C. The crude residue obtained is purified by chromatography at atmospheric pressure on 20 g of silica (0.063–0.22 mm) contained in a column 2.5 cm in diameter, eluting with dichloromethane and collecting 10 cm$^3$ fractions. The fractions containing only the desired product are combined and concentrated to dryness under reduced pressure (2.7 kPa) at 40° C. for 2 hours. 204 mg of 4α-acetoxy-2α-benzoyloxy-5β,20-epoxy-1β,13α-dihydroxy-10β-(1-propyl)oxy-9-oxo-7β-trifluoromethanesulphonyloxy-11-taxene are thus obtained in the form of a brown foam.

4α-Acetoxy-2α-benzoyloxy-5β,20-epoxy-1β,7β,13α-trihydroxy-10β-(1-propyl)oxy-9-oxo-11-taxene (or 10β-(1-propyl)oxy-10-deacetoxybaccatin III) may be prepared in the following way:

To a solution of 591 mg of 4α-acetoxy-2α-benzoyloxy-5β,20-epoxy-1β-hydroxy-10β-(1-propyl)oxy-9-oxo-7β,13α-bis(triethylsilyloxy)-11-taxene in 6 cm$^3$ of dichloromethane, kept under an argon atmosphere and at a temperature in the region of 20° C., are added 9 cm$^3$ of hydrogen fluoride-triethylamine complex (3HF.Et$_3$N). After 21 hours at a temperature in the region of 20° C., the reaction mixture is diluted with 40 cm$^3$ of dichloromethane and poured onto a suspension of 40 cm$^3$ of supersaturated aqueous sodium hydrogen carbonate solution, maintained at a temperature in the region of 0° C. After dilution with 10 cm$^3$ of distilled water and separation of the phases by settling, the aqueous phase is reextracted with twice 20 cm$^3$ of diethyl ether. The organic phases are combined, washed with 20 cm$^3$ of distilled water, 20 cm$^3$ of saturated aqueous sodium chloride solution, dried over magnesium sulphate, filtered on a sinter funnel and concentrated to dryness under reduced pressure (2.7 kPa) at a temperature in the region of 40° C. 370 mg of a pale yellow foam are thus obtained, which product is purified by chromatography at atmospheric pressure on 35 g of silica (0.063–0.2 mm) contained in a column 2.5 cm in diameter, eluting with a methanol/ dichloromethane mixture (2/98 by volume), collecting 15 cm³ fractions. The fractions containing only the desired product are combined and concentrated to dryness under reduced pressure (2.7 kPa) at 40° C. for 2 hours. 236.2 mg of 4α-acetoxy-2α-benzoyloxy-5β,20-epoxy-1β,7β,13α-trihydroxy-10β-(1-propyl)oxy-9-oxo-11-taxene are thus obtained in the form of a white solid, the characteristics of which are as follows:

¹H NMR spectrum (400 MHz; CDCl₃; chemical shifts δ in ppm; coupling constants J in Hz): 1.08 (s, 3H: CH₃); 1.19 (s, 3H: CH₃); 1.29 (t, J=7.5, 3H: CH₃ of the ethyl); 1.38 (d, J=9, 1H: OH at 7); 1.59 (s, 1H: OH at 1); 1.69 (s, 3H: CH₃); 1.82 and 2.62 (2 mts, 1H each: CH₂ at 6); 2.02 (d, J=5, 1H: OH at 13); 2.08 (s, 3H: CH₃); 2.30 (s, 3H: COCH₃); 2.32 (d, J=9, 2H: CH₂ at 14); 3.56 and 3.67 (2 mts, 1H each: OCH₂ of the ethyl); 3.98 (d, J=7, 1H: H at 3); 4.18 and 4.33 (2 d, J=8.5, 1H each: CH₂ at 20); 4.30 (mt, 1H: H at 7); 4.90 (mt, 1H: H at 13); 4.99 (dd, J=10 and 1.5, 1H: H at 5); 5.05 (s, 1H: H at 10); 5.66 (d, J=7, 1H: H at 2); 7.49 (t, J=7.5, 2H: OCOC₆H₅ meta-H); 7.63 (t, J=7.5, 1H: OCOC₆H₅ para-H); 8.12 (d, J=7.5, 2H: OCOC₆H₅ ortho-H).

4α-Acetoxy-2α-benzoyloxy-5β,20-epoxy-1β-hydroxy-10β-(1-propyl)oxy-9-oxo-7β,13α-bis(triethylsilyloxy)-11-taxene (or 10β-(1-propyl)oxy-10-deacetoxy-7,13-bis(triethylsilyl)baccatin III) may be obtained in the following way:

To a solution of 1 g of 4α-acetoxy-2α-benzoyloxy-5β,20-epoxy-1β,10β-dihydroxy-9-oxo-7β,13α-bis(triethylsilyloxy)-11-taxene in 3 cm³ of iodoethane and 4 cm³ of dimethylformamide, kept under an argon atmosphere and at a temperature in the region of 20° C., are added portionwise 93 mg of sodium hydride at a concentration of 50% by weight in liquid petrolatum. The solution is kept stirring for 17 hours at a temperature in the region of 20° C. and 93 mg of sodium hydride at a concentration of 50% by weight in liquid petrolatum are then added portionwise. After 50 minutes at a temperature in the region of 20° C., the reaction mixture is diluted with 100 cm³ of ethyl acetate and 10 cm³ of saturated aqueous ammonium chloride solution. The organic phase, separated out by settling, is washed six times with 10 cm³ of distilled water and then 10 cm³ of saturated aqueous sodium chloride solution, dried over magnesium sulphate, filtered on a sinter funnel and concentrated to dryness under reduced pressure (2.7 kPa) at a temperature in the region of 40° C. 1.2 g of a yellow foam are thus obtained, which product is purified by chromatography at atmospheric pressure on 150 g of silica (0.063–0.2 mm) contained in a column 3.5 cm in diameter, eluting with an ethyl acetate/dichloromethane mixture (2/98 and then 5/95 by volume), collecting 15 cm³ fractions. The fractions containing only the desired products are combined and concentrated to dryness under reduced pressure (0.27 kPa) at 40° C. for 2 hours. 379.2 mg of 4α-acetoxy-2α-benzoyloxy-5β,20-epoxy-1β,10β-dihydroxy-9-oxo-7β,13α-bis(triethylsilyloxy)-11-taxene in the form of a pale yellow foam and 430 mg of 4α-acetoxy-2α-benzoyloxy-5β,20-epoxy-1β-hydroxy-10β-(1-propyl)oxy-9-oxo-7β,13α-bis(triethylsilyloxy)-11-taxene in the form of a white foam are thus obtained, the characteristics of which are as follows:

¹H NMR spectrum (400 MHz; CDCl₃; chemical shifts δ in ppm; coupling constants J in Hz): 0.57 and 0.70 (2 mts, 6H each: CH₂ of the ethyl); 0.97 and 1.03 (2 t, J=7.5, 9H each: CH₃ of the ethyl); 1.13 (s, 3H: CH₃); 1.20 (s, 3H: CH₃); 1.29 (t, J=7.5, 3H: CH₃ of the ethoxy at 10); 1.58 (s, 1H: OH at 1); 1.66 (s, 3H: CH₃); 1.89 and 2.58 (2 mts, 1H each: CH₂ at 6); 2.03 (s, 3H: CH₃); 2.13 and 2.23 (2 dd, J=16 and 9, 1H each: CH₂ at 14); 2.30 (s, 3H: COCH₃); 3.53 (mt, 2H: CH₂ of ethoxy at 10); 3.84 (d, J=7, 1H: H at 3); 4.15 and 4.30 (2 d, J=8.5, 1H each: CH₂ at 20); 4.43 (dd, J=11 and 6.5, 1H: H at 7); from 4.90 to 5.00 (mt, 2H: H at 13 and H at 5); 5.01 (s, 1H: H at 10); 5.61 (d, J=7, 1H: H at 2); 7.48 (t, J=7.5, 2H: OCOC₆H₅ meta-H); 7.61 (t, J=7.5, 1H: OCOC₆H₅ para-H); 8.10 (d, J=7.5, 2H: OCOC₁H₅ ortho-H).

The novel products of general formula (I) in which Z represents a radical of general formula (II) exhibit significant inhibitory activity on abnormal cell proliferation and possess therapeutic properties which make it possible to treat patients having pathological conditions associated with abnormal cell proliferation. The pathological conditions include the abnormal cell proliferation of malignant or benign cells of various tissues and/or organs comprising, without any limitation being implied, muscle, bone or conjunctive tissues, the skin, the brain, the lungs, the sexual organs, the lymphatic or renal systems, breast or blood cells, the liver, the digestive system, the pancreas and the thyroid or adrenal glands. These pathological conditions may also include psoriasis, solid tumours, cancers of the ovary, breast, brain, prostate, colon, stomach, kidney or testicles, Kaposi's sarcoma, cholangiocarcinoma, choriocarcinoma, neuroblastoma, Wilms' tumour, Hodgkin's disease, melanomas, multiple myelomas, chronic lymphocytic leukaemias and acute or chronic granulocytic lymphomas. The novel products according to the invention are particularly useful for treating cancer of the ovary. The products according to the invention may be used for preventing or delaying the appearance or reappearance of the pathological conditions or for treating these pathological conditions.

The products according to the invention may be administered to a patient in various forms adapted to the chosen route of administration, which is preferably the parenteral route. Administration via the parenteral route comprises intravenous, intraperitoneal, intramuscular or subcutaneous administrations. Intraperitoneal or intravenous administration is more particularly preferred.

The present invention also comprises the pharmaceutical compositions which contain at least one product of general formula (I) in a sufficient amount suitable for use in human or veterinary therapy. The compositions may be prepared according to the usual methods, using one or more pharmaceutically acceptable adjuvants, vehicles or excipients. Suitable vehicles include diluents, sterile aqueous media and various non-toxic solvents. The compositions are preferably provided in the form of aqueous solutions or suspensions, of injectable solutions which may contain emulsifying agents, dyes, preserving agents or stabilizing agents.

The choice of adjuvants or excipients may be determined by the solubility and the chemical properties of the product, the particular mode of administration and good pharmaceutical practice.

Aqueous or non-aqueous sterile solutions or suspensions are used for parenteral administration. For the preparation of non-aqueous solutions or suspensions, natural vegetable oils such as olive oil, sesame oil or liquid paraffin, or injectable organic esters such as ethyl oleate, may be used. The aqueous sterile solutions may consist of a solution of a pharmaceutically acceptable salt in water. The aqueous solutions are suitable for intravenous administration provided that the pH is appropriately adjusted and that the solution is made isotonic, for example with a sufficient amount of sodium chloride or glucose. The sterilization may be performed by heating or by any other means which does not adversely affect the composition.

It is clearly understood that all the products entering into the compositions according to the invention must be pure and non-toxic in the amounts used.

The compositions may contain at least 0.01% of therapeutically active product. The amount of active product in a composition is such that a suitable dosage may be prescribed. The compositions are preferably prepared such that a single dose contains from 0.01 to 1000 mg approximately of active product for administration via the parenteral route.

The therapeutic treatment may be carried out concurrently with other therapeutic treatments including antineoplastic drugs, monoclonal antibodies, immunotherapies or radiotherapies or biological-response modifiers. The response modifiers include, without any limitation being implied, lymphokines and cytokines such as interleukins, interferons (α, β or δ) and TNF. Other chemotherapeutic agents which are useful in the treatment of disorders due to abnormal cell proliferation include, without any limitation being implied, alkylating agents such as nitrogen mustards, for instance mechloretamine, cyclophosphamide, melphalan and chlorambucil, alkyl sulphonates, for instance busulphan, nitrosoureas, for instance carmustine, lomustine, semustine and streptozocin, trazenes, for instance dacarbazine, antimetabolites, for instance folic acid analogues such as methotrexate, pyrimidine analogues, for instance fluorouracil and cytarabine, purine analogues, for instance mercaptopurine and thioguanine, natural products such as vinca alkaloids, for instance vinblastine, vincristine and vendesine, epipodophyllotoxins, for instance etoposide and teniposide, antibiotics, for instance dactinomycin, daunorubicin, doxorubicin, bleomycin, plicamycin and mitomycin, enzymes, for instance L-asparaginase, various agents, for instance platinum coordination complexes such as cisplatin, substituted ureas such as hydroxyurea, methylhydrazine derivatives, for instance procarbazine, adrenocorticoid suppressants, for instance mitotane and aminoglutethymide, hormones and antagonists, for instance adrenocorticosteroids, for instance prednisone, progestins, for instance hydroxyprogesterone caproate, methoxyprogesterone acetate and megestrol acetate, oestrogens, for instance diethylstilbestrol and ethynylestradiol, antioestrogens such as tamoxifen, and androgens, for instance testosterone propionate and fluoxymesterone.

The doses used for implementing the methods according to the invention are those which permit a prophylactic treatment or a maximum therapeutic response. The doses vary according to the form of administration, the particular product selected and the personal characteristics of the subject to be treated. In general, the doses are those which are therapeutically effective for the treatment of disorders due to abnormal cell proliferation. The products according to the invention may be administered as often as necessary in order to obtain the desired therapeutic effect. Some patients may respond rapidly to relatively high or low doses, and then require low or zero maintenance doses. Generally, low doses will be used at the start of the treatment and, if necessary, increasingly high doses will be administered until an optimum effect is obtained. For other patients, it may be necessary to administer maintenance doses 1 to 8 time a day, preferably 1 to 4 times, according to the physiological needs of the patient in question. It is also possible that, for certain patients, only one to two daily administrations are necessary.

In man, the doses are generally between 0.01 and 200 mg/kg. Via the intraperitoneal route, the doses will generally be between 0.1 and 100 mg/kg and preferably between 0.5 and 50 mg/kg and even more specifically between 1 and 10 mg/kg. Via the intravenous route, the doses are generally between 0.1 and 50 mg/kg and preferably between 0.1 and 5 mg/kg and even more specifically between 1 and 2 mg/kg. It is understood that, in order to choose the most suitable dosage, the route of administration, the patient's weight, general state of health and age, and all the factors which may influence the effectiveness of the treatment, will have to be taken into account.

The example which follows illustrates a composition according to the invention.

EXAMPLE 40 mg of the product obtained in Example 1 are dissolved in 1 cm$^3$ of Emulphor EL 620 and 1 cm$^3$ of ethanol, and the solution is then diluted by addition of 18 cm$^3$ of physiological serum.

The composition is administered by infusion over 1 hour by introduction into physiological solution.

We claim:

1. A taxoid of general formula:

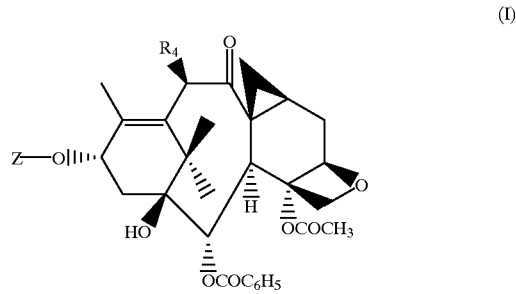

in which:

Z represents a hydrogen atom or a radical of general formula:

in which:

R$_1$ represents a benzoyl radical unsubstituted or substituted with one or more atoms or radicals, which may be identical or different, selected from halogen atoms, alkyl radicals containing 1 to 4 carbon atoms, alkoxy radicals containing 1 to 4 carbon atoms and trifluoromethyl, thenoyl or furoyl radicals, or a radical R$_2$—O—CO— in which:

R$_2$ represents an alkyl radical containing 1 to 8 carbon atoms, an alkenyl radical containing 2 to 8 carbon atoms, an alkynyl radical containing 3 to 8 carbon atoms, a cycloalkyl radical containing 3 to 6 carbon atoms, a cycloalkenyl radical containing 4 to 6 carbon atoms or a bicycloalkyl radical containing 7 to 10 carbon atoms, these radicals being unsubstituted or substituted with one or more substituents selected from halogen atoms, hydroxyl radicals, alkoxy radicals containing 1 to 4 carbon atoms, dialkylamino radicals in which each alkyl pair contains 1 to 4 carbon atoms, piperidino, morpholino or 1-piperazinyl radicals unsubstituted or substituted at the 4 position with an alkyl radical containing 1 to 4 carbon atoms or with a phenylalkyl radical in which the alkyl part contains 1 to 4 carbon atoms, cycloalkyl radicals containing 3 to 6 carbon atoms, cycloalkenyl radicals containing 4 to 6 carbon atoms, phenyl radicals unsubstituted or substituted with one or more atoms or radicals selected from halogen atoms, alkyl radicals containing 1 to 4 carbon atoms or alkoxy radicals containing 1 to 4 carbon atoms, cyano or carboxyl radicals or alkoxycarbonyl radicals in which the alkyl portion contains 1 to 4 carbon atoms, a phenyl or α- or β-naphthyl radical unsubstituted or substituted with one or more atoms or radicals selected from halogen atoms, alkyl radicals containing 1 to 4 carbon atoms alkoxy radicals containing 1 to 4 carbon atoms or a 5-membered aromatic heterocyclic radical, or a saturated heterocyclic radical containing 4 to 6 carbon atoms substituted or substituted with one or more alkyl radicals containing 1 to 4 carbon atoms;

$R_3$ represents a straight or branched alkyl radical containing 1 to 8 carbon atoms, a straight or branched alkenyl radical containing 2 to 8 carbon atoms, a straight or branched alkynyl radical containing 2 to 8 carbon atoms, a cycloalkyl radical containing 3 to 6 carbon atoms, a phenyl or α- or β-naphthyl radical unsubstituted or substituted with one or more atoms or radicals selected from halogen atoms, alkyl, alkenyl, alkynyl, aryl, aralkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, alkylcarbamoyl, dialkylcarbamoyl, cyano, nitro and trifluoromethyl radicals, or a 5-membered aromatic heterocycle containing one or more hetero atoms, which may be identical or different, selected from nitrogen, oxygen or sulphur atoms and unsubstituted or substituted with one or more substituents, which may be identical or different, selected from halogen atoms, alkyl, aryl, amino, alkylamino, dialkylamino, alkoxycarbonylamino, acyl, arylcarbonyl, cyano, carbamoyl, alkylcarbamoyl, dialkylcarbamoyl or alkoxycarbonyl radicals, wherein in the substituents of the phenyl, α- or β-naphthyl radicals and aromatic heterocyclic radicals, the alkyl radicals and the alkyl portions of the other radicals contain 1 to 4 carbon atoms the alkenyl and alkynyl radicals contain 2 to 8 carbon atoms and the aryl radicals are phenyl or α- or β-naphthyl radicals;

$R_4$ represents an alkoxy radical containing 1 to 6 carbon atoms in a straight or branched chain, an alkenyloxy radical containing 3 to 6 carbon atoms in a straight or branched chain, an alkynyloxy radical containing 3 to 6 carbon atoms in a straight or branched chain, a cycloalkyloxy radical containing 3 to 6 carbon atoms, a cycloalkenyloxy radical containing 3 to 6 carbon atoms unsubstituted or substituted with one or more substituents selected from halogen atoms, alkoxy radicals containing 1 to 4 carbon atoms, an alkylthio radical containing 1 to 4 carbon atoms, a carboxyl radical, an alkyloxycarbonyl radical in which the alayl portion contains 1 to 4 carbon atoms, a cyano radical a carbamoyl radical, an N-alkylcarbamoyl or N,N-dialkylcarbamoyl radical in which each alkyl portion contains 1 to 4 carbon atoms or forms, with the nitrogen atom to which it is attached, a 5- or 6-membered saturated heterocyclic radical which may contain a second hetero atom selected from oxygen, sulphur or nitrogen atoms unsubstituted or substituted with an alkyl radical containing 1 to 4 carbon atoms or a phenyl radical or a phenylalkyl radical in which the alkyl portion contains 1 to 4 carbon atoms.

2. The taxoid according to claim 1 in which Z represents a hydrogen atom or a radical of general formula (II) in which $R_1$ represents a benzoyl radical or a radical $R_2$—O—CO— in which $R_2$ represents a tert-butyl radical; $R_3$ represents an alkyl radical containing 1 to 6 carbon atoms, an alkenyl radical containing 2 to 6 carbon atoms, a cycloalkyl radical containing 3 to 6 carbon atoms, a phenyl radical unsubstituted or substituted with one or more atoms or radicals, which may be identical or different, selected from halogen atoms, alkyl, alkoxy, dialkylamino, acylamino, alkoxycarbonylamino or trifluoromethyl radicals, 2- or 3-furyl, 2- or 3-thienyl, and 2-, 4- or 5-thiazolyl radicals; and $R_4$ represents a straight or branched alkyloxy radical containing 1 to 6 carbon atoms.

3. The taxoid according to claim 1 in which Z represents a hydrogen atom or a radical of general formula (II) in which $R_1$ represents a benzoyl radical or a radical $R_2$—O—CO— in which $R_2$ represents a tert-butyl radical;

$R_3$ represents an isobutyl, isobutenyl, butenyl, cyclohexyl, phenyl, 2-furyl, 3-furyl, 2-thienyl, 3-thienyl, 2-thiazolyl, 4-thiazolyl or 5-thiazolyl radical; and $R_4$ represents a methoxy, ethoxy or propoxy radical.

4. A process for the preparation of a taxoid according to claim 1, comprising esterifying a product of general formula:

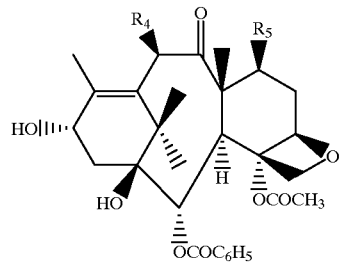

(III)

in which $R_4$ is defined as in claim 1 and $R_5$ represents a trifluoromethanesulphonyloxy radical or forms a bond with the carbon atom of the α-methyl radical, so as to form a cyclopropane ring, using an acid or a derivative of an acid of general formula:

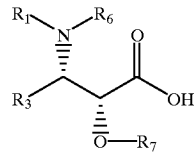

(IV)

in which $R_1$ and $R_3$ are defined as in claim 1, $R_6$ represents a hydrogen atom and $R_7$ represents a protecting group for the hydroxyl function, or $R_6$ and $R_7$ together form a 5- or 6-membered saturated heterocycle, to obtain an ester of general formula:

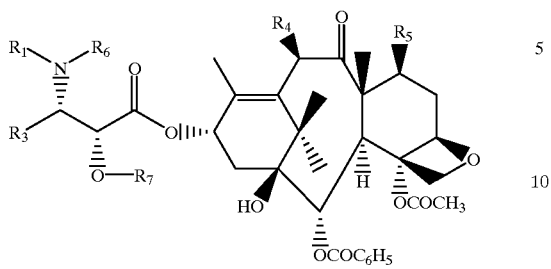

(V)

in which $R_1$, $R_3$, $R_4$, $R_5$, $R_6$ and $R_7$ are defined as above, followed by replacing the protecting groups $R_7$ or $R_6$ and $R_7$ with hydrogen atoms and, when $R_5$ represents a trifluoromethanesulphonyloxy radical, this radical is removed so as to form a cyclopropane ring with the carbon atom of the α-methyl radical.

5. A process according to claim 4, wherein the esterification is carried out using an acid of general formula (IV) in the presence of a coupling agent and an activating agent in an organic solvent at a temperature between −10 and 90° C.

6. A process according to claim 4, wherein the esterification is carried out using an acid of general formula (IV) in symmetrical anhydride form, working in the presence of an activating agent in an organic solvent at a temperature between 0 and 90° C.

7. A process according to claim 4, wherein the esterification is carried out using the acid of general formula (IV) in halide form with an aliphatic or aromatic acid, in the presence of a base, working in an organic solvent at a temperature between 0 and 80° C.

8. The process according to claim 4, wherein the protecting groups $R_7$ and/or $R_6$ and $R_7$ are replaced with hydrogen atoms, in the following manner:

1) when $R_6$ represents a hydrogen atom and $R_7$ represents a protecting group for the hydroxyl function, the protecting groups are replaced by hydrogen atoms using an inorganic acid or organic acid used alone or as a mixture, working in an organic solvent selected from alcohols, ethers, esters, aliphatic hydrocarbons, halogenated aliphatic hydrocarbons, aromatic hydrocarbons or nitriles, at a temperature between −10 and 60° C., 2) when $R_6$ and $R_7$ together form an oxazolidine ring of general formula:

(VI)

in which $R_1$ is defined as in claim 1, $R_8$ and $R_9$, which may be identical or different, represent a hydrogen atom or an alkyl radical containing 1 to 4 carbon atoms or an aralkyl radical in which the alkyl portion contains 1 to 4 carbon atoms and the aryl portion represents a phenyl radical unsubstituted or substituted with one or more alkoxy radicals containing 1 to 4 carbon atoms, or an aryl radical unsubstituted or substituted with one or more alkoxy radicals containing 1 to 4 carbon atoms, or alternatively $R_8$ represents an alkoxy radical containing 1 to 4 carbon atoms, a trihalomethyl radical or a phenyl radical substituted with a trihalomethyl radical and $R_9$ represents a hydrogen atom, or alternatively $R_8$ and $R_9$ form, together with the carbon atom to which they are attached, a 4- to 7-membered ring, the protecting group formed by $R_6$ and $R_7$ is replaced by hydrogen atoms in the following way:

a) when $R_1$ represents a tert-butoxycarbonyl radical, $R_8$ and $R_9$, which may be identical or different, represent an alkyl, aralkyl or aryl radical, or alternatively $R_8$ represents a trihalomethyl radical or a phenyl radical substituted with a trihalomethyl radical, and $R_9$ represents a hydrogen atom, or alternatively $R_8$ and $R_9$ together form a 4- to 7-membered ring, the ester of general formula (V) is treated with an inorganic or organic acid, where appropriate in an organic solvent, to give a product of general formula:

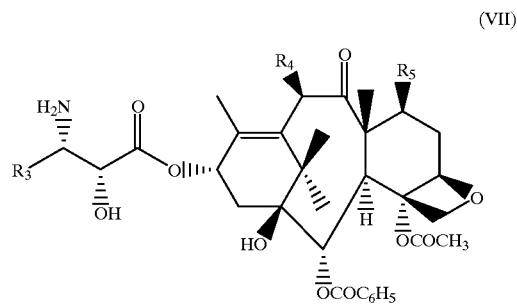

(VII)

in which $R_3$, $R_4$ and $R_5$ are defined as in claim 1, which is acylated using benzoyl chloride in which the phenyl ring is unsubstituted or substituted by means of, thenoyl chloride, furoyl chloride or a product of general formula:

$$R_2\text{—O—CO—X} \qquad \text{(VIII)}$$

in which $R_2$ is defined as in claim 1 and X represents a halogen atom or a residue —O—$R_2$ or —O—CO—O—$R_2$, in order to obtain a product of general formula (I) in which Z represents a radical of general formula (II);

b) when $R_1$ represents an unsubstituted or substituted benzoyl radical, a thenoyl radical, a furoyl radical or a radical $R_2$O—CO— in which $R_2$ is defined as in claim 1, $R_8$ represents a hydrogen atom, an alkoxy radical containing 1 to 4 carbon atoms or a phenyl radical substituted with one or more alkoxy radicals containing 1 to 4 carbon atoms and $R_9$ represents a hydrogen atom, the protecting group formed by $R_6$ and $R_7$ is replaced by hydrogen atoms in the presence of an inorganic acid or an organic acid used alone or as a mixture, in stoichiometric or catalytic amount, working in an organic solvent chosen from alcohols, ethers, esters, aliphatic hydrocarbons, halogenated aliphatic hydrocarbons and aromatic hydrocarbons, at a temperature between −10 and 60° C.

9. The process according to claim 4, wherein the radical $R_5$, representing a trifluoromethanesulphonyloxy radical, is eliminated in order to form a bond with the carbon atom of the α-methyl radical using an alkaline metal halide, an alkaline metal azide or an ammonium salt, working in an organic solvent selected from ethers, nitriles or aliphatic esters, or mixtures thereof, at a temperature between 20° C. and the boiling point of the reaction mixture.

10. A process for the preparation of a taxoid of general formula:

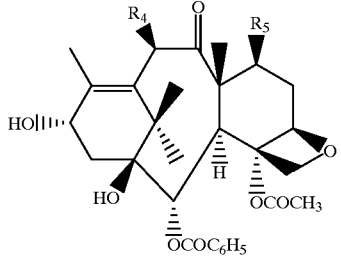

(III)

in which $R_4$ is defined as in claim 1 and $R_5$ represents a trifluoromethanesulphonyloxy radical or forms a bond with the carbon atom of the α-methyl radical, wherein 10-deacetylbaccatin III of formula:

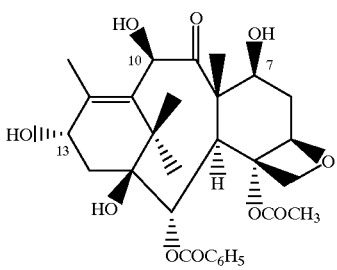

(IX)

is treated with a silyl halide of general formula:

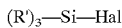

$(R')_3$—Si—Hal     (X)

in which the symbols R', which may be identical or different, represent an alkyl radical containing 1 to 4 carbon atoms unsubstituted or substituted with a phenyl radical, or a phenyl radical, in order to obtain a product of general formula:

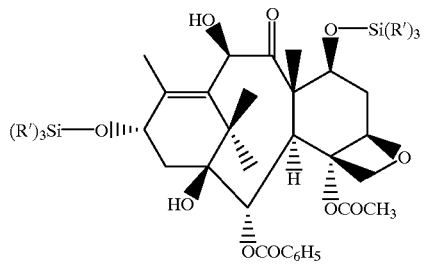

(XI)

in which R' is defined as above, which product is treated with a product of general formula:

$R'_4$—$X_1$     (XII)

in which $R'_4$ is such that $R'_4$—O is identical to $R_4$ as in claim 1 and $X_1$ represents a halogen atom or a reactive ester residue, to obtain a product of general formula:

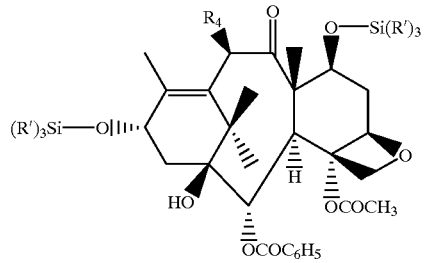

(XIII)

in which R' and $R_4$ are defined as above, the silyl protecting groups of which are replaced by hydrogen atoms to obtain a product of general formula:

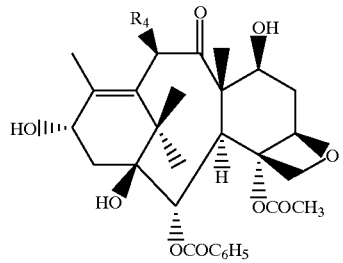

(XIV)

in which $R_4$ is defined as above, which product is treated with a trifluoromethanesulphonic acid derivative to obtain a product of general formula (III) in which $R_5$ represents a trifluoromethanesulphonyloxy radical.

11. 4α-Acetoxy-2α-benzoyloxy-5β,20-epoxy-1β-hydroxy-10β-methoxy-7β,8β-methylene-9-oxo-19-nor-11-taxen-13α-yl (2R,3S)-3-tert-butoxycarbonylamino-2-hydroxy-3-phenylpropionate.

12. 4α-Acetoxy-2α-benzoyloxy-5β,20-epoxy-1β-hydroxy-10β-ethoxy-7β,8β-methylene-9-oxo-19-nor-11-taxen-13α-yl (2R,3S)-3-tert-butoxycarbonylamino-2-hydroxy-3-phenylpropionate.

13. 4α-Acetoxy-2α-benzoyloxy-5β,20-epoxy-1β-hydroxy-10β-(1-propyl)oxy-7β,8β-methylene-9-oxo-19-nor-11-taxen-13α-yl (2R,3S)-3-tert-butoxycarbonylamino-2-hydroxy-3-phenylpropionate.

14. A pharmaceutical composition, comprising at least one according to claim 1 in which Z represents a radical of general formula (II), in combination with one or more pharmaceutically acceptable diluents or adjuvants and which may contain one or more compatible and pharmacologically active compounds.

15. A pharmaceutical composition comprising at least one taxoid according to claim 11, in combination with one or more pharmaceutically acceptable diluents or adjuvants and which may contain one or more compatible and pharmacologically active compounds.

16. A pharmaceutical composition comprising at least one taxoid according to claim 12, in combination with one or more pharmaceutically acceptable diluents or adjuvants and which may contain one or more compatible and pharmacologically active compounds.

17. A pharmaceutical composition comprising at least one product according to claim 13, in combination with one or more pharmaceutically acceptable diluents or adjuvants and which may contain one or more compatible and pharmacologically active compounds.

18. The taxoid according to claim 1, wherein in the definition of $R_1$, said 5-membered aromatic heterocyclic radical is selected from a furyl radical and thienyl radicals.

19. The process according to claim 7, wherein the acid of general formula (IV) is in the form of the mixed anhydride.

20. The process according to claim 7, wherein the aliphatic or aromatic acid is prepared in situ.

21. The process according to claim 8, wherein in the definition of $R_8$ and $R_9$, the aryl radical is a phenyl radical.

22. The process according to claim 8, wherein the treatment of the ester of general formula (IV) is carried out in an alcohol.

23. The process according to claim 8, wherein the protecting group formed from $R_6$ and $R_7$ is replaced at a temperature between 15 and 30° C.

24. The process according to claim 10, wherein the reactive ester residue is a sulphuric or sulphonic ester residue.

25. The process according to claim 10, wherein the product of general formula (III) is treated with an alkali metal halide or an alkali metal azide or an ammonium salt, working in an organic solvent selected from ethers, nitriles and aliphatic esters, or mixtures thereof, at a temperature between 20° C. and the boiling point of the reaction mixture, to obtain a product of general formula (III) in which $R_5$ forms a bond with the carbon atom of the α-methyl radical.

* * * * *